United States Patent [19]

Costanzo et al.

[11] Patent Number: 5,242,942

[45] Date of Patent: Sep. 7, 1993

[54] ANTICONVULSANT FRUCTOPYRANOSE CYCLIC SULFITES AND SULFATES

[75] Inventors: Michael J. Costanzo, Ivyland; Bruce E. Maryanoff, New Hope, both of Pa.

[73] Assignee: McNeilab, Inc., Spring House, Pa.

[21] Appl. No.: 874,875

[22] Filed: Apr. 28, 1992

[51] Int. Cl.$^5$ .................... A61K 31/39; C07D 497/14
[52] U.S. Cl. .................... 514/439; 514/23; 549/31; 549/336; 549/396; 536/54
[58] Field of Search .................... 549/31, 34, 396; 514/439, 445, 456, 23; 536/54

[56] References Cited

U.S. PATENT DOCUMENTS

| | | | |
|---|---|---|---|
| 4,075,351 | 2/1978 | Hirsch | 514/517 |
| 4,513,006 | 4/1985 | Maryanoff, II et al. | 558/48 |
| 4,591,601 | 5/1986 | Maryanoff et al. | 514/462 |
| 4,792,569 | 12/1988 | Maryanoff et al. | 514/517 |

OTHER PUBLICATIONS

B. Maryanoff et al., (I), *J. Med. Chem*, 30 (5) pp. 880–887 (1987).

*Primary Examiner*—Mark Russell
*Attorney, Agent, or Firm*—Ralph R. Palo

[57] ABSTRACT

Compounds of the general formula (I):

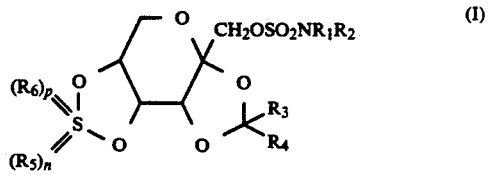

wherein $R_1$, $R_2$, $R_3$, $R_4$, $R_5$, $R_6$, n and p are as herein defined; exhibit anticonvulsant activity and are thus useful in the treatment of conditions such as epilepsy. Compounds of this class are also useful for the treatment of glaucoma, peptic ulcers, hypertension, congestive heart failure and other types of edema. Furthermore, pharmaceutical compositions containing a compound of formula (I) as well as methods for their use and novel intermediates are disclosed.

29 Claims, No Drawings

ANTICONVULSANT FRUCTOPYRANOSE CYCLIC SULFITES AND SULFATES

BACKGROUND OF THE INVENTION

Sulfamate derivatives having useful pharmaceutical activity in the areas of epilepsy, glaucoma, peptic ulcers and male infertility are disclosed in U.S. Pat. Nos. 4,075,351, 4,513,006, 4,591,601 and 4,792,569.

Most recently, a sulfamate derivative known as topiramate was discovered and is under development by McNeilab, Inc. the assignee of the present invention, for the treatment of epilepsy. This sulfamate derivative is disclosed in U.S. Pat. No. 4,513,006 and described in *J. Med. Chem.* 1987, 30, 880.

It is an object of the present invention to describe novel sulfamate derivatives with potent anticonvulsant activity.

SUMMARY OF THE INVENTION

Compounds of the following formula (I):

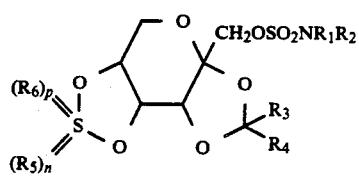

wherein $R_1$, $R_2$, $R_3$, $R_4$, $R_5$, $R_6$, n and p are as herein defined, possess anticonvulsant activity in mammals and are thus useful in the treatment of CNS disorders such as epilepsy. Compounds of formula (I) are also useful for treating glaucoma or peptic ulcers. In addition, compounds of formula (I) are diuretic, hence they are useful in the treatment of hypertension, congestive heart failure and other types of edema. The present invention comprises the compounds of formula (I), pharmaceutical compositions containing one or more of the compounds of formula (I) and methods for the treatment or prevention of convulsions, peptic ulcers, glaucoma, hypertension, congestive heart failure and other types of edema, using such compounds. Compounds useful as intermediates to prepare compounds of formula (I) are also included in this invention.

DETAILED DESCRIPTION OF THE INVENTION

Compounds of the present invention are represented by the following formula (I):

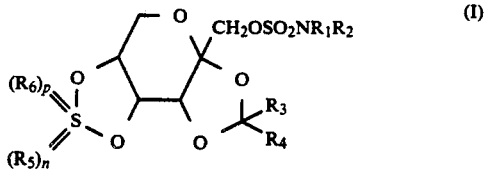

wherein
$R_1$ and $R_2$ are the same or different and are selected from hydrogen, $C_1$-$C_{12}$ alkyl, $C_3$-$C_{10}$ cycloalkyl, allyl, benzyl, $CH_2$—($C_1$-$C_4$ perfluoroalkyl), or are taken together with N to represent an azido group; i.e., $R_1$ and $R_2$ represent $N_3$;

$R_3$ and $R_4$ are the same or different and are selected from hydrogen, $C_1$-$C_6$ alkyl, or are taken together to form a cyclopentyl or cyclohexyl ring;

$R_5$ and $R_6$ may be the same or different and are selected from oxygen or $NR_7$; where $R_7$ is selected from hydrogen, $C_1$-$C_4$ alkyl, $C_1$-$C_4$ perfluoroalkyl, arenesulfonyl, $C_1$-$C_4$ alkoxycarbonyl or benzyloxycarbonyl.

Each of n and p is either zero or one, provided that n and p are not both equal to zero at the same time. A lone pair of electrons is designated when either n or p are equal to zero. For example:

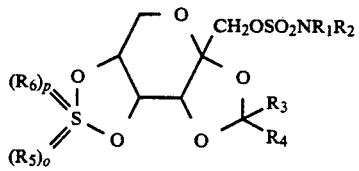 designates 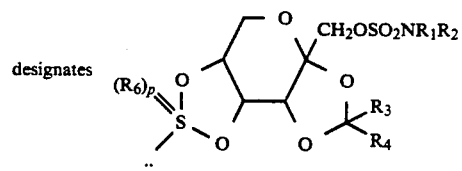

As used herein alkyl, alkoxy and perfluoroalkyl include straight and branched chains. For example, alkyl radicals include methyl, ethyl, propyl, isopropyl, n-butyl, isobutyl, sec-butyl, t-butyl, n-pentyl, 2-methyl-3-butyl, 1-methylbutyl, 2-methylbutyl, neopentyl, n-hexyl, 1-methylpentyl, 3-methylpentyl and n-octyl. Perfluoroalkyl radicals are defined as the previously described straight or branched chain alkyl radicals in which all of the hydrogen atoms have been replaced with fluorine atoms, e.g. trifluoromethyl, pentafluoroethyl, heptafluoropropyl, etc.. Alkoxy radicals are oxygen ethers formed from the previously described straight or branched chain alkyl groups. Arenesulfonyl radicals include, for example, phenylsulfonyl, o-toluenesulfonyl, m-toluenesulfonyl, p-toluenesulfonyl (abbreviated as "Ts"), 1-naphthalenesulfonyl, 2-naphthalenesulfonyl, and 5-dimethylamino-1-naphthalenesulfonyl.

Cyclic sulfites are designated when n equals one, p equals zero, and $R_5$ is oxygen and also when n equals zero, p equals one and $R_6$ is oxygen. Cyclic sulfates are designated when n equals one, p equals one, $R_5$ is oxygen and $R_6$ is oxygen. Cyclic imidosulfites are designated when n equals one, p equals zero and $R_5$ is $NR_7$ and also when n equals zero and p equals one and $R_6$ is $NR_7$. Cyclic imidosulfates are designated when n equals one, p equals one, $R_5$ is oxygen and $R_6$ is $NR_7$ and also when n equals one, p equals one, $R_5$ is $NR_7$ and $R_6$ is oxygen. Cyclic diimidosulfates are designated when n equals one, p equals one, $R_5$ equals $NR_7$ and $R_6$ equals $NR_7$.

The system of stereodescription developed by Cahn, Ingold and Prelog and described in *Angew. Chem. Int. Ed. Engl.* 1966, 5, 385 is used herein to describe the the absolute stereochemistry of stereogenic sulfur atoms. For example, the structure of (R)-2,3-O-(1-methylethylidene)-4,5-O-sulfinyl-β-D-fructopyranose sulfamate is shown below:

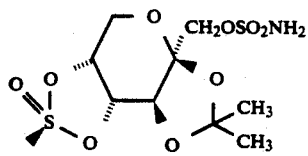

Compounds of formula (I) can exist in the β-D-fructopyranose and the β-L-fructopyranose absolute configurations. As used herein, the β-D-fructopyranose absolute configuration is defined as:

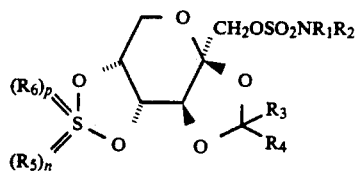

and the β-L-fructopyranose absolute configuration is defined as:

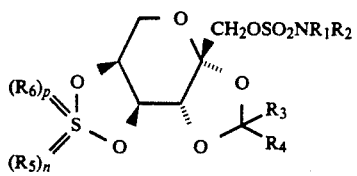

Preferred compounds of formula (I) are those wherein the compounds are in the β-D-fructopyranose absolute configuration wherein; $R_1$ and $R_2$ are as defined above; $R_3$ and $R_4$ are methyl; $R_5$ and $R_6$ are oxygen; n and p are equal to one. Particularly preferred compounds of formula (I) are those in the β-D-fructopyranose absolute configuration wherein; $R_1$ and $R_2$ are hydrogen or methyl; $R_3$ and $R_4$ are methyl; $R_5$ and $R_6$ are oxygen; n and p are equal to one. Examples of specific compounds of formula (I) are:

2,3-O-(1-methylethylidene)-4,5-O-sulfonyl-β-D-fructopyranose sulfamate, i.e. where the compound is in the β-D-fructopyranose absolute configuration, $R_1$ and $R_2$ are hydrogen, $R_3$ and $R_4$ are methyl, $R_5$ and $R_6$ are oxygen, and n and p are equal to one;

2,3-O-(1-methylethylidene)-4,5-O-sulfonyl-β-L-fructopyranose sulfamate, i.e. where the compound is in the β-L-fructopyranose absolute configuration, $R_1$ and $R_2$ are hydrogen, $R_3$ and $R_4$ are methyl, $R_5$ and $R_6$ are oxygen, and n and p are equal to one;

2,3-O-(1-methylethylidene)-4,5-O-sulfonyl-β-D-fructopyranose methylsulfamate, i.e. where the compound is in the β-D-fructopyranose absolute configuration, $R_1$ is hydrogen, $R_2$ is methyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose butylsulfamate, i.e. where the compound is in the β-D-fructopyranose absolute configuration, $R_1$ is hydrogen, $R_2$ is n-butyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose ethylsulfamate, i.e. where the compound is in the β-D-fructopyranose absolute configuration, $R_1$ is hydrogen, $R_2$ is ethyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose octylsulfamate, i.e. where the compound is in the β-D-fructopyranose absolute configuration, $R_1$ is hydrogen, $R_2$ is n-octyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose 2-propenylsulfamate, i.e. where the compound is in the β-D-fructopyranose absolute configuration, $R_1$ is hydrogen, $R_2$ is allyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose phenylmethylsulfamate; i.e. where the compound is in the β-D-fructopyranose absolute configuration, $R_1$ is hydrogen, $R_2$ is benzyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose cyclopropylsulfamate, i.e. where the compound is in the β-D-fructopyranose absolute configuration, $R_1$ is hydrogen, $R_2$ is cyclopropyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose cyclobutylsulfamate, i.e. where the compound is in the β-D-fructopyranose absolute configuration, $R_1$ is hydrogen, $R_2$ is cyclobutyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose cyclooctylsulfamate, i.e. where the compound is in the β-D-fructopyranose absolute configuration, $R_1$ is hydrogen, $R_2$ is cycloctyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose (2,2,2-trifluoroethyl)sulfamate, i.e. where the compound is in the β-D-fructopyranose absolute configuration, $R_1$ is hydrogen, $R_2$ is 2,2,2-trifluoroethyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose dimethylsulfamate, i.e. where the compound is in the β-D-fructopyranose absolute configuration, $R_1$ and $R_2$ are methyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose diethylsulfamate, i.e. where the compound is in the β-D-fructopyranose absolute configuration, $R_1$ and $R_2$ are ethyl, $R_3$ and $R_4$ are methyl, $R_5$ and $R_6$ are oxygen, and n and p are equal to one;

2,3-O-(1-methylethylidene)-4,5-O-sulfonyl-β-D-fructopyranose azidosulfate, i.e. where the compound is in the β-D-fructopyranose absolute configuration, $R_1$ and $R_2$ are taken together with the nitrogen of formula (I) to represent an azido ($N_3$) group, $R_3$ and $R_4$ are methyl, $R_5$ and $R_6$ are oxygen, and n and p are equal to one;

(S)-2,3-O-(1-methylethylidene)-4,5-O-sulfinyl-β-D-fructopyranose sulfamate, i.e. where the compound is in the β-D-fructopyranose absolute configuration, R₁ and R₂ are hydrogen, R₃ and R₄ are methyl, R₅ is oxygen, R₆ is a lone pair of electrons, n is equal to one, p is equal to zero, and the absolute stereochemistry at the sulfite sulfur is (S);

(R)-2,3-O-(1-methylethylidene)-4,5-O-sulfinyl-β-D-fructopyranose sulfamate, i.e. where the compound is in the β-D-fructopyranose absolute configuration, R₁ and R₂ are hydrogen, R₃ and R₄ are methyl, R₅ is a lone pair of electrons, R₆ is oxygen, n is equal to zero, p is equal to one, and the absolute stereochemistry at the sulfite sulfur is (R);

2,3-O-(1-ethylpropylidene)-4,5-O-sulfonyl-β-D-fructopyranose sulfamate, i.e. where the compound is in the β-D-fructopyranose absolute configuration, R₁ and R₂ are hydrogen, R₃ and R₄ are ethyl, R₅ and R₆ are oxygen, and n and p are equal to one;

2,3-O-(1-methylethylidene)-4,5-O-[N-(4-methylbenzenesulfonyl)imidosulfinyl]-β-D-fructopyranose sulfamate, i.e. where the compound is in the β-D-fructopyranose absolute configuration, R₁ and R₂ are hydrogen, R₃ and R₄ are methyl, R₅ is NR₇, R₆ is a lone pair of electrons, n is equal to one, p is equal to zero, and R₇ is p-toluenesulfonyl;

2,3-O-(1-methylethylidene)-4,5-O-[N-(4-methylbenzenesulfonyl)imidosulfonyl]-β-D-fructopyranose sulfamate, i.e. where the compound is in the β-D-fructopyranose absolute configuration, R₁ and R₂ are hydrogen, R₃ and R₄ are methyl, R₅ is NR₇, R₆ is oxygen, n is equal to one, p is equal one, and R₇ is p-toluenesulfonyl;

2,3-O-(cyclohexylidene)-4,5-O-sulfonyl-β-D-fructopyranose sulfamate, i.e. where the compound is in the β-D-fructopyranose absolute configuration, R₁ and R₂ are hydrogen, R₃ and R₄ are taken together with carbon to which they are both bonded to represent a cyclohexane ring, R₅ and R₆ are oxygen, and n and p are equal to one;

(S)-4,5-O-[N-(1,1-dimethylethoxycarbonyl)imidosulfinyl]-2,3-O-(1-methylethylidene)-β-D-fructopyranose sulfamate, i.e. where the compound is in the β-D-fructopyranose absolute configuration, R₁ and R₂ are hydrogen, R₃ and R₄ are methyl, R₅ is NR₇, R₆ is a lone pair of electrons, n is equal to one, p is equal to zero, R₇ is t-butoxycarbonyl, and the absolute stereochemistry at the imidosulfite sulfur is (S);

and the pharmaceutically acceptable salts thereof.

Included within the scope of this invention are the various individual anomers, diastereomers and enantiomers as well as mixtures thereof. Such compounds are included within the definition of formula (I). In addition, the compounds of this invention also include any pharmaceutically acceptable salts, for example: alkali metal salts, such as sodium and potassium; ammonium salts; monoalkylammonium salts; dialkylammonium salts; trialkylammonium salts; tetraalkylammonium salts; and tromethamine salts. Hydrates and other solvates of the compound of the formula (I) are included within the scope of this invention.

The compounds of the formula (I) may be synthesized by the following general methods:

In the first method, a compound of the formula (II);

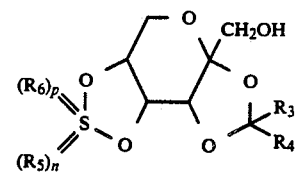

is reacted with a sulfamoyl chloride of the formula $ClSO_2NR_1R_2$, where $R_1$ and $R_2$ are as defined above, in the presence of a base such as potassium t-butoxide, sodium hydride, triethylamine, or pyridine at a temperature of about −60° to about 25° C. in an aprotic solvent such as toluene, ethyl acetate, tetrahydrofuran, acetonitrile or dimethylformamide thereby producing the compound of formula (I). For example:

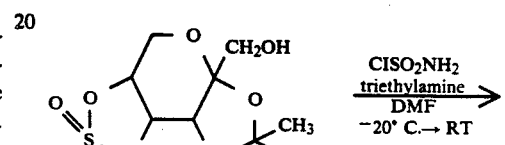

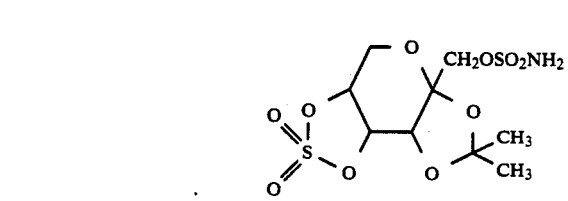

Compounds of the formula (I) where $R_1$ or $R_2$ are alkyl groups may also be prepared by the alkylation of a sulfamate salt of the formula (I); i.e., where either $R_1$ or $R_2$ is sodium, potassium, tetramethylammonium, etc. with reactive alkylating agents, such as methyl iodide or benzyl bromide, under anhydrous conditions in a solvent such as tetrahydrofuran, dimethylsulfoxide or dimethylformamide at a temperature of about −40° to about 110° C. For example:

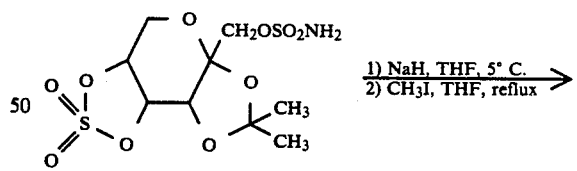

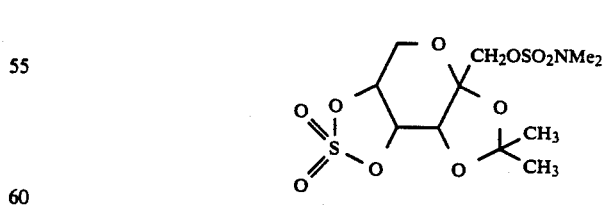

In a third method to produce compounds of formula (I), a compound of formula (II) is reacted with sulfuryl chloride in the presence of pyridine or triethylamine at a temperature of about −60° to about 25° C. in an aprotic solvent such as diethyl ether, ethyl acetate, dichloromethane or toluene to produce a chlorosulfate of the formula (III).

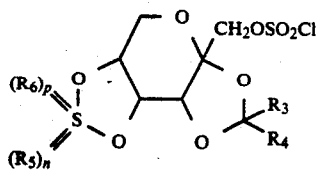
(III)

The chlorosulfate of formula (III) is subsequently reacted with an amine of the formula $R_1R_2NH$, wherein $R_1$ and $R_2$ are as described above, under anhydrous conditions at a temperature of about $-60°$ to about $25°$ C. in an aprotic solvent such as tetrahydrofuran, acetonitrile or dichloromethane to produce a compound of formula (I). For example:

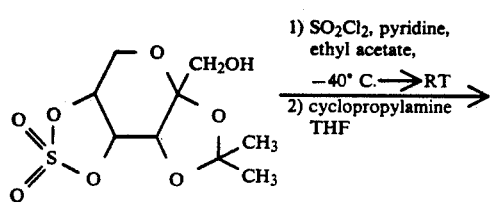

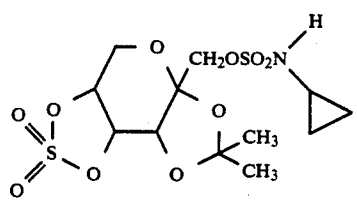

A fourth method to produce compounds of formula (I) involves reacting a diol of the formula (IV):

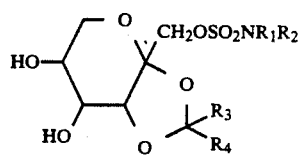
(IV)

with sulfuryl chloride in the presence of pyridine or triethylamine at a temperature of about $-78°$ to about $25°$ C. in an aprotic solvent such as ethyl acetate, toluene, or dichloromethane to produce the bis-chlorosulfate of formula (V).

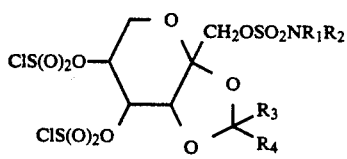
(V)

For example:

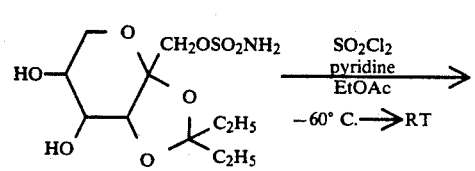

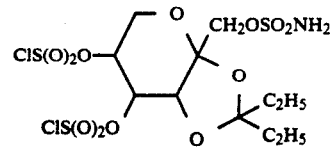

Dechlorosulfation of the bis-chlorosulfate of formula (V) with a weak base such as $NaHCO_3$ or pyridine in an alcohol such as methanol or ethanol at about $-40°$ to about $25°$ C. yields cyclic sulfate compounds of the formula (I). For example:

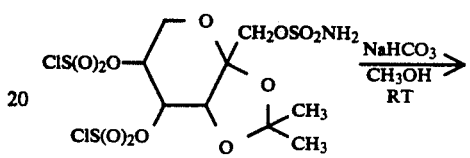

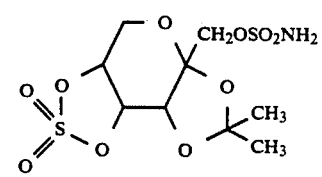

A method to prepare cyclic sulfate and imidosulfate compounds of the formula (I) involves the oxidation of the corresponding cyclic sulfites or imidosulfites of the formula (I) with $RuCl_3$ and $NaIO_4$ according to the method of Sharpless et al. in *Tetrahedron Lett.* 1989, 30, 655. For example:

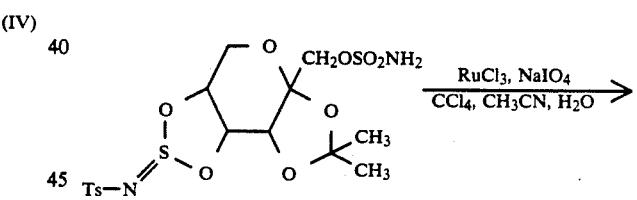

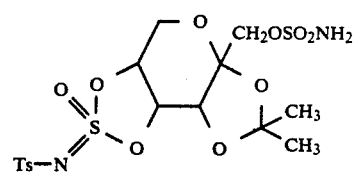

Other strong oxidants, such as $OsO_4$, $KMnO_4$, dialkyl dioxiranes, diperfluoroalkyl dioxiranes or alkylperfluoroalkyl dioxiranes may also be used to effect this transformation. For example:

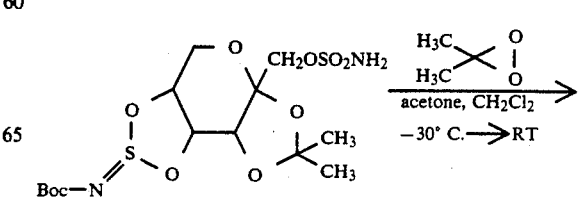

-continued

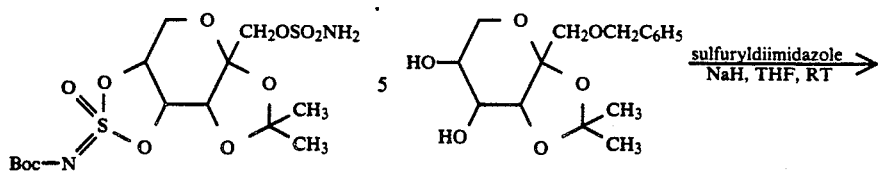

Cyclic sulfate and imidosulfate compounds of formula (I) may also be prepared from benzyl cyclic sulfites and imidosulfites of the formula (VI).

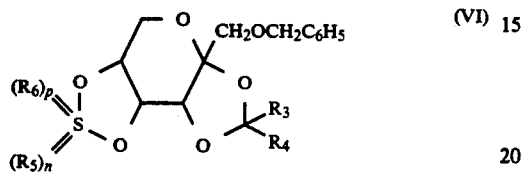

Oxidation of cyclic sulfites and imidosulfites of formula (VI) with $RuO_4$ or other strong oxidants produces the corresponding benzyl cyclic sulfates and imidosulfates. Debenzylation of these benzyl cyclic sulfates and imidosulfates to the corresponding cyclic sulfates and imidosulfates of the formula (II) can be effected with hydrogen in the presence of a noble metal catalyst, such as $Pd(OH)_2$ on carbon, in an alcoholic solvent such as ethanol or methanol at about 25° to about 60° C.
For example:

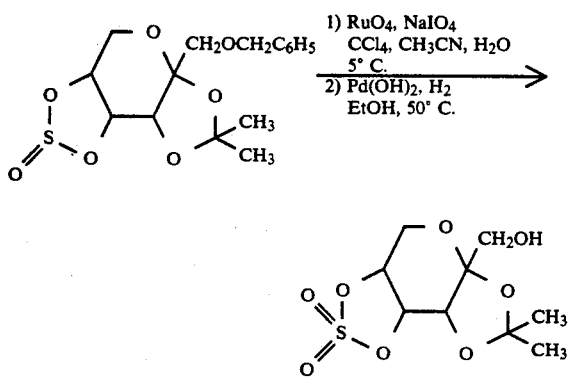

Conversion of the resulting compounds of the formula (II) to the corresponding compounds of formula (I) may be accomplished as previously described herein.

Alternatively, benzyl cyclic sulfates and diimidosulfates of the formula (VI) may be prepared by the treatment of diols of formula (VII) with an excess of sodium hydride in tetrahydrofuran at room temperature followed by reaction with sulfuryldiimidazole or $NR_7$-substituted diimidosulfuryl fluorides, respectively.

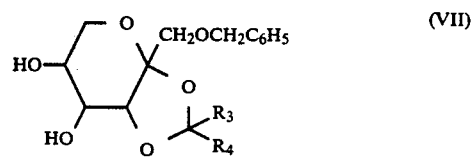

For example:

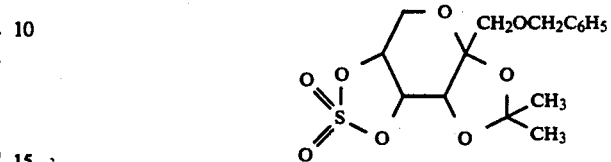

Conversion of the benzyl cyclic sulfate and diimidosulfate compounds of the formula (VI) to the corresponding cyclic sulfate compounds of formula (I) may be accomplished as described in the preceding method.

Cyclic sulfites and imidosulfites of formula (I) can also be prepared by the reaction of diols of formula (III) with thionyl chloride or $NR_7$-substituted imidothionyl chlorides, respectively, under anhydrous conditions in aprotic solvents such as diethyl ether, dioxane, tetrahydrofuran, or in toluene or dichloromethane at about $-40°$ C. to about 110° C., with or without the presence of a base, such as pyridine or triethylamine. For example:

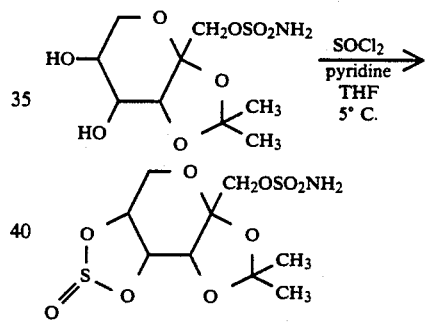

Similarly, benzyl cyclic sulfites and imidosulfites of the formula (VI) can be prepared by the reaction of diols of the formula (VII) with thionyl chloride or $NR_7$-substituted imidothionyl chloride, respectively, in ethereal solvents such as diethyl ether, dioxane, and tetrahydrofuran or in toluene or dichloromethane at about $-40°$ to about 110° C., with or without the presence of a base, such as pyridine or triethylamine. Oxidative debenzylation with N-bromosuccinimide according to the method of Binkley et al. in *J. Org. Chem.* 1990, 55, 378, provides the corresponding cyclic sulfites and imidosulfites of the formula (II). Conversion of these alcohols to the cyclic sulfite and imidosulfite compounds of formula (I) may be accomplished as previously described herein. For example:

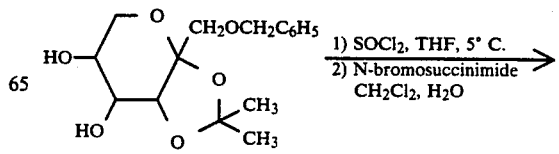

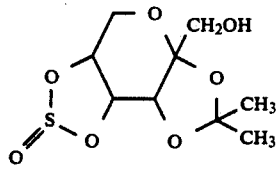

Still another method to prepare cyclic sulfates of formula (I) involves reaction of a triol of the formula (VIII):

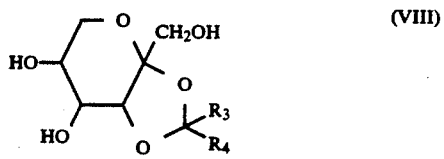

with sulfuryl chloride as described by Martin et al. in *Can. J. Chem.* 1982, 60, 1857, in an aprotic solvent such as diethyl ether, ethyl acetate, toluene or dichloromethane to produce a tris-chlorosulfate of the formula (IX):

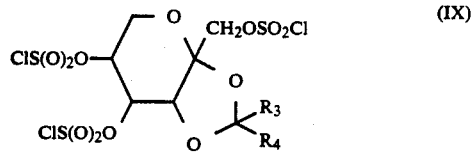

Dechlorosulfation of the tris-chlorosulfate with a base such as $K_2CO_3$, $NaHCO_3$ or pyridine, at about $-40°$ to about $25°$ C. in an alcohol such as methanol or ethanol gives a cyclic sulfate of formula (II), which may be converted to the corresponding compounds of formula (I) as previously described herein. For example:

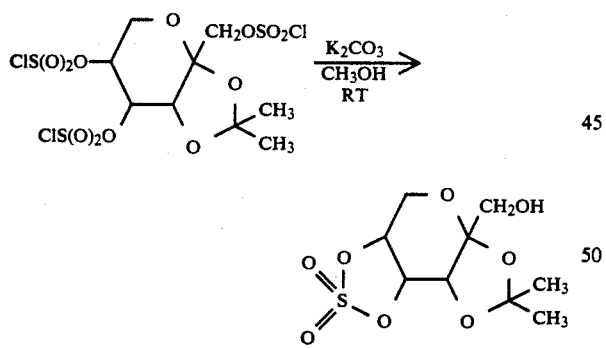

The starting materials required to synthesize compounds of formula (I) may be prepared by methods known to those skilled in the art of organic synthesis. For example, novel compounds of the formulas (II) and (IX) may be obtained by the methods analogous to those described by Martin et al. in *Can. J. Chem.* 1982, 60, 1857. Novel diols of the formula (IV) may be prepared by the procedures analogous to those described by Maryanoff et al. in *J. Med. Chem.* 1987, 30, 880. Triols of the formula (VIII) may be obtained as described by the method of Wolfrom et al. in *J. Am. Chem. Soc.* 1950, 72, 4544. Diols of the formula (VII) may be prepared by the method described by Zervas et al. in *Chem. Ber.* 1933, 66, 1698. The requisite $NR_7$-substituted imidothionyl chlorides and $NR_7$-substituted diimidosulfuryl fluorides may be prepared by the procedures analogous to those described by Levchenko et al. in *Zh. Org. Khimi.* 1979, 15, 2485 and Glemser et al. in *Angew. Chem. Int. Ed. Engl.* 1980, 19, 408, respectively. The starting 2,3:4,5-bis-O-(alkylidene)-β-D-fructopyranoses and 2,3:4,5-bis-O-(cycloalkylidene)-β-D-fructopyranoses may be prepared by the method reported by Brady in *Carbohydr. Res.* 1970, 15, 35 or by the procedure described in U.S. Pat. No. 4,659,809.

Pharmaceutically acceptable salts of the compounds of formula (I) can be prepared by reacting the sulfamate of formula (I) with the appropriate base and recovering the salt. For example:

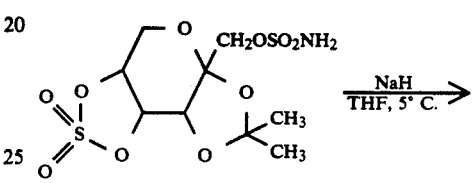

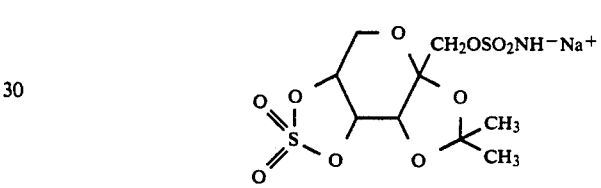

Compounds of the formulas (II), (III), (IV), (V), (VI) and (IX):

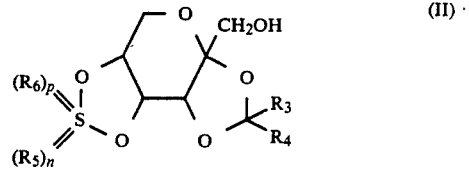

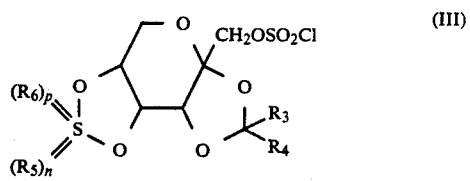

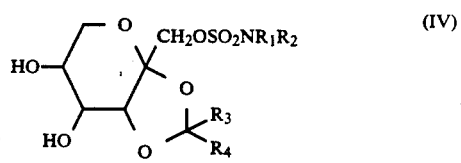

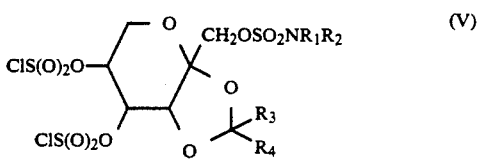

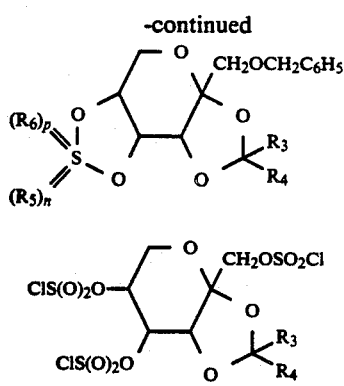

wherein $R_1$, $R_2$, $R_3$, $R_4$, $R_5$, $R_6$, n and p are defined as previously described for the compounds of formula (I); with the proviso that $R_3$ and $R_4$ can not both be methyl at the same time for compounds of the formulas (II) and (IX) and when $R_1$ and $R_2$ are both hydrogen for compounds of the formula (IV). Compounds of the formulas (II), (III), (IV), (V), (VI) and (IX) as defined here are useful as intermediates to prepare compounds of the formula (I) and are included in this invention.

The compounds of formula (I) are particularly useful as anticonvulsant agents in mammals including humans. The anticonvulsant activity of the subject compounds was determined using a standard "maximal electroshock test" (MES). In this test, activity is indicated by a block of the toxic extensor seizure caused by application of an electric shock to mice via corneal electrodes, as described by Swinyard et al. in *J. Pharmacol. Expt. Ther.* 1952, 106, 319, and recorded as % block. A more recent description of current anticonvulsant drug screening is given by Swinyard in *Epilepsia* 1978, 19, 409. The anticonvulsant activity of the compounds of this invention tested according to the Swinyard 1952 method is shown in the following Table I.

In the test, albino male CRS-CD1 mice weighing between 18–25 g were used in all experiments (obtained from Charles River). They were allowed food and water ad libitum and were used only once. The electroshock apparatus and the corneal electrodes were purchased from Wahlquist Instrument Company, Salt Lake City, Utah.

Maximal electroshock seizures were induced by the delivery of a 60 Hertz (Hz) current of 50 milliamps (mA) intensity to the mouse through corneal electrodes for 0.2 seconds as originally described by Swinyard et al. (1952). This stimulus intensity is approximately 4 to 6 times the current producing 100% tonic extensor convulsions. During the validation of the MES test, the duration of the various seizure components following maximal electroshock were measured as follows: hindleg tonic flexion was measured from the time of the application of the stimulus to the time of onset of hindleg tonic extension (i.e. when the hindlegs deviate by greater than an angle of 90° from the torso), hindleg tonic extensor was measured from the time of extensor thrust to the onset of generalized clonus, and terminal clonus was measured from the beginning to the end of bilateral rhythmic clonic jerking. Mortality was also recorded. The duration of each seizure component agreed well with the values previously reported by Tedeschi et al. in *J. Pharmacol. Expt. Ther.* 1955, 116, 107. The corneal electrodes were concave so that saline could be applied to the electrodes to reduce mortality. If this procedure is followed, mortality should always be less than 40% in control mice. Thus, at an electroshock stimulus of 60 Hz, 50 mA and 0.2 seconds duration, the order of convulsive components and the percentage of control animals displaying the behaviors should be as follows: tonic flexion (100%), tonic extension (100%) and clonus (100%) with less than 40% mortality.

For testing compounds, the abolition of the tonic extensor component was the endpoint. Animals were dosed orally (PO) with either vehicle or test drug and at a specified time were given a maximal electric shock through corneal electrodes blotted with saline (as described above). A minimum of 10 animals were used per group and the percentage of animals in the group without tonic hindlimb extension recorded. Determination of $ED_{50}$ values (that dose of drug inhibiting 50% of the tonic extensor seizures) is shown below in Table I.

TABLE I
ANTICONVULSANT ACTIVITY DATA

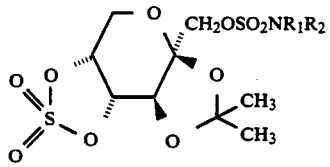

| Compound of Example | $R_1$ | $R_2$ | dosage (mg/kg, PO) | MES Test (mouse) % Block or $ED_{50}$ at 4 hr |
|---|---|---|---|---|
| 1 | H | H | | $ED_{50} = 6.3$ mg/kg |
| 2 | L-isomer of Example 1 | | 75 | 80 |
| 3 | H | $CH_3$ | 10 | 100 |
| 4 | H | $C_4H_9$ | 35 | 100 |
| 5 | H | $C_2H_5$ | 10 | 100 |
| 6 | H | octyl | 75 | 100 |
| 7 | H | allyl | 10 | 70 |
| 8 | H | benzyl | 75 | 100 |
| 9 | H | cyclopropyl | 10 | 90 |
| 10 | H | cyclobutyl | 10 | 90 |
| 11 | H | cyclooctyl | 75 | 30 |
| 12 | H | $CH_2CF_3$ | 10 | 40 |
| 13 | $CH_3$ | $CH_3$ | 10 | 70 |
| 14 | $C_2H_5$ | $C_2H_5$ | 10 | 10 |

TABLE I-continued
ANTICONVULSANT ACTIVITY DATA

| Compound of Example | $R_1$ | $R_2$ | dosage (mg/kg, PO) | MES Test (mouse) % Block or $ED_{50}$ at 4 hr |
|---|---|---|---|---|
| 15 | | $N_2$ | 35 | 100 |
| 16 | | (CH$_2$OSO$_2$NH$_2$, CH$_3$, CH$_3$ structure) | 75 | 40 |
| 17 | | (CH$_2$OSO$_2$NH$_2$, CH$_3$, CH$_3$ structure) | 35 | 90 |
| 18 | | (CH$_2$OSO$_2$NH$_2$, C$_2$H$_5$, C$_2$H$_5$ structure) | 75 | 100 |
| 19 | | (Ts—N, CH$_2$OSO$_2$NH$_2$, CH$_3$, CH$_3$ structure) | 300 | 80 |
| 20 | | (Ts—N, CH$_2$OSO$_2$NH$_2$, CH$_3$, CH$_3$ structure) | 300 | 75 |

Ts = p-toluenesulfonyl.

For treating epilepsy, a compound of formula (I) may be employed at a daily dosage in the range of about 10 mg to about 2000 mg, usually in 1 to 4 divided dosages, for an average adult human. A unit dosage would contain about 2.5 mg to about 500 mg of the active ingredient.

In general, compounds of formula (I) may be used in treating epilepsy in mammals including humans in a manner similar to that used for phenytoin. Medical aspects of the treatment of epilepsy are described in greater detail by Rall and Schleifer in *Goodman and Gilman's The Pharmacological Basis of Therapeutics*, 8th ed.; Goodman Gilman, A.; Rall, T. W.; Nies, A. S.; Taylor, P., Eds.; Pergamon Press: New York, 1990; pp 436–462.

Compounds of formula (I) also exhibit gastric antisecretory activity and thus are useful in the treatment of peptic ulcers in mammals, including humans. The gastric antisecretory activity of the compounds shown in Table II was determined by the pylorus-ligated rat test described by Shay et al. in *Gastroenterol.* 1954, 26, 906. In this method, male Charles River Sprague-Dawley derived rats weighing 150–300 grams were deprived of food but not water for 18-24 hours prior to use. Water was withheld during the experiment, however. The rats were weighed, lightly anesthetized with ether and the pylorus ligated according to the method of Shay et al., supra. The treatment or vehicle control was then administered intraperitoneally (IP) or orally (PO). When administered by the IP route, the administration was done 30 minutes before ligation. When administered by the PO route, the administration was done prior to ligation (about ½ to 3 hours before). Rats were housed two per cage and sacrificed with carbon dioxide 3 hours after ligation. Their stomachs were removed, rinsed, and contents emptied into a graduated centrifuge tube. The tubes were centrifuged, the volume of gastric juice was recorded, and any samples obviously contaminated by feces, food or blood were eliminated. A 1 mL aliquot of gastric juice was titrated with 0.1N NaOH to a pH of 7.0–7.4. The volume of gastric juice secreted, the acid concentration, and the product of the volume times the concentration, i.e. the total amount of acid secreted, were measured. The total acid output was calculated by multiplying the volume of gastric juices collected times the hydrogen ion concentration (amount of NaOH added to a sample to reach a pH of 7.0–7.4) and dividing that value by 10. The mean value of the total acid output for a control group of rats was then subtracted from the mean value of the total acid output for the group of rats tested at the same dose. That value was then divided by the mean value of total acid output for the control group and the resulting number was multiplied by 100 to provide a Percent Inhibition value, which values are reported in Table II. The PO value was determined statistically as the dose at which a 50% inhibition would be realized.

and shaken in a protolytic enzyme solution to promote disassociation of the hepatocytes. The dissociated hepatocytes were then washed in a cold saline solution and used for determination of carbonic anhydrase activity.

The carbonic anhydrase inhibition activity can be detected by an acceleration of the rate of disappearance of $C^{16}O^{18}O$ (mass 46) from the reaction mixture, which contained $^{18}O$-labeled 25 mM aqueous $NaHCO_3$ at 25° C., pH 7.4. The mass 46 peak $C^{16}O^{18}O$ decreases because of exchange with the $^{16}O$ pool in water. The mass spectrometer was set to record the mass 46 peak and the mass 44 peak alternately every 15 seconds. The continuous readout of the mass 44 peak gives a continuous record of the constancy of the pH of the reaction medium since the height of the mass 44 peak is very sensitive to pH. The pH of the medium was read from the pH meter and used to calibrate the mass 44 peaks at regular intervals.

An 8 mL glass chamber, with openings for a pH electrode and sample insertion, was used for continuous mass spectrophotometric measurement of $C^{16}O^{16}O$ (mass 44) and $C^{16}O^{18}O$ (mass 46) dissolved in aqueous bicarbonate buffer. The ion source of the mass spectrometer (Consolidated Electronics, Pasadena, Calif., model 21-601A) was separated from the reaction mixture by a thin Teflon membrane supported by a sintered glass disc. The pH was constantly monitored by a com-

TABLE II
GASTRIC ANTISECRETORY ACTIVITY

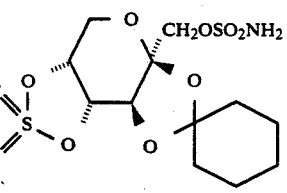

| Compound of Example | $R_1$ | $R_2$ | Route | Percent Inhibition of Total Acid Output (200 mg/kg or $ED_{50}$) |
|---|---|---|---|---|
| 1 | H | H | PO | $ED_{50}$ = 20 mg/kg |
| 9 | H | cyclopropyl | IP | 87% |
| 11 | H | cyclooctyl | IP | 50% |
| 15 | $N_2$ | | IP | 96% |
| 21 | (structure with $CH_2OSO_2NH_2$ and cyclohexyl) | | IP | 27% |

For treating peptic ulcers, a compound of formula (I) may be employed at a daily dosage in the range of about 40 mg to about 4000 mg, usually in 1 to 4 divided dosages, for an average adult human. A unit dosage would contain about 10 mg to about 1000 mg of the active ingredient.

Compounds of formula (I) are also inhibitors of carbonic anhydrase, and as such, are useful in the treatment of glaucoma. Such activity may be determined by mass spectrometry using the $^{18}O$-exchange technique described by Dodgson and Forster in J. Appl. Physiol. 1983, 55, 1293. Specifically, this assay was conducted by first killing the male rats and then removing their livers. Their livers were placed in a cold physiological saline solution. The liver tissue was then minced with scissors bination glass pH electrode (Radiometer model gK 2641C). The temperature of the chamber was regulated at 25° C. by circulating water through a jacket. The response time of the entire system to a change of $CO_2$ partial pressure in the reaction mixture, including mixing time and mass spectrometer memory, was three seconds.

To determine the carbonic anhydrase inhibition activity, 0.1 mL of male rat hepatocyte suspension was added to the reaction chamber containing 3 mL of incubation medium, which was adjusted to pH 7.4 and comprised of 118 mM naCl, 4.7 mM KCl, 1.2 mM $KH_2PO_4$, 1.2 mM $MgSO_4$, 2.4 mM ethylenebis(oxyethylenenitrilo)tetraacetic acid (EGTA), 5 mM glucose, and 25 mM $^{18}$O-labeled NaHCO$_3$ in water. The $^{18}$O-labeled NaHCO$_3$ was prepared by the exchange reaction of unlabeled bicarbonate (Fisher Scientific) and water enriched with 1.5% H$_2^{18}$O (Bio-Rad Laboratories). The carbonic anhydrase inhibition activity of a test compound at a concentration of 250 μM was determined on a mixture of the incubation medium and a solution of the test compound in N,N-dimethylformamide.

The compound of Example 1, i.e. 2,3-O-(1-methylethylidene)-4,5-O-sulfonyl-β-D-fructopyranose sulfamate, was tested for carbonic anhydrase inhibition using this assay on disrupted male rate hepatocytes at 37° C., pH 7.4, in 25 mM aqueous NaHCO$_3$ (1% labelled with $^{18}$O). Maximal inhibition of all hepatocyte carbonic anhydrase was observed for the compound of Example 1 at a concentration of 250 μM; i.e. a significant acceleration of the rate of disappearance of C$^{16}$O$^{18}$O from the reaction mixture was observed.

Evidence for the inhibition of carbonic anhydrase by compounds of the formula (I) can also be obtained by a diuresis study, such as described by A. Weiner in *Goodman and Gilman's The Pharmacological Basis of Therapeutics*, 8th ed.; Goodman Gilman, A.; Rall, T. W.; Nies, A. S.; Taylor, P., Eds.; Pergamon Press: New York, 1990; pp 716–718. An increase in urine akalinity accompanied with an increase in water intake and urine output provides an indirect indication of carbonic anhydrase inhibition activity. Male Wistar rats having a weight of 250–300 g were dosed orally (PO) and housed in cages that allowed for the quantitative measure of fluid intake and urine output. Water intake and urine output were measured at 24 hours versus control, whereas urine pH, obtained via pH meter, was measured at 4 and 24 hours versus control. The results of this study, which are the average of five animals, are reported below in Table III. These data indicate that selected examples of compounds of the formula (I) significantly increase water intake, urine output as well as urine alkalinity, providing indirect evidence of useful carbonic anhydrase inhibition. Such data is also an indication of the usefulness of the compounds of formula (I) as diuretics in the treatment of hypertension, congestive heart failure and other types of edema. The determination of suitable dosages for such compounds for the treatment of hypertension and congestive heart failure and other types of edema is within the skill of the art.

TABLE III

Rat Diuresis Data

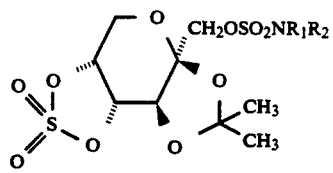

| Compound of Example | R$_1$ | R$_2$ | Dose (mg/kg) | Time (hours) | Water Intake (mL)* | Urine Output (mL)* | Urine pH* |
|---|---|---|---|---|---|---|---|
| 1 | H | H | 6.3 | 4 | — | — | 8.99 |
|   |   |   |     | 24 | 24.0 | 28.3 | 7.03 |
| 3 | H | CH$_3$ | 2.7 | 4 | — | — | 9.02 |
|   |   |   |     | 24 | 23.6 | 28.8 | 6.78 |
| 5 | H | C$_2$H$_5$ | 1.2 | 4 | — | — | 9.03 |
|   |   |   |     | 24 | 15.8 | 19.9 | 6.41 |
| 9 | H | cyclopropyl | 2.5 | 4 | — | — | 9.02 |
|   |   |   |     | 24 | 27.8 | 33.2 | 7.26 |
| 13 | CH$_3$ | CH$_3$ | 2.1 | 4 | — | — | 8.93 |
|   |   |   |     | 24 | 21 | 23.2 | 6.81 |
| control |   |   |   | 4 | — | — | 6.98 |
|   |   |   |     | 24 | 15.0 | 17.6 | 6.43 |

*Average of five animals.

The relationship between the treatment of glaucoma and carbonic anhydrase inhibition is described by Stein et al. in the *American Journal of Ophthalmology* 1983, 95, 222. For the treatment of glaucoma, a compound of formula (I) may be administered systemically, e.g. by oral or parenteral routes as described below. Alternatively, the compounds of the formula (I) may be administered topically in the eye, for example, in a mineral oil solution or suspension, or aqueous suspension. The compounds of the formula (I) would be administered, topically in the eye or systemically, in a daily dosage of about 0.4 mg to about 750 mg per day for an average adult human, with the dosage being administered about 1 to 4 times per day. A unit dosage would contain about 0.1 mg to about 750 mg of the active ingredient.

The compounds of formula (I) preferably are administered in the form of a pharmaceutical composition. To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral unit dosage form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for purposes such as aiding solubility or for preservation, may be included. Injectable suspensions may also be prepared, in which case appropriate liquid carriers, suspending agents and the like may be employed.

It is especially advantageous to formulate the aforementioned pharmaceutical compositions in unit dosage form for ease of administration and uniformity of dosage. The term "unit dosage form" as used in the specification and claims herein refers to physically discrete units suitable as unit dosages, each unit containing a predetermined quantity of active ingredient calculated to produce the desired therapeutic effect in association with the required pharmaceutical carrier.

The pharmaceutical compositions herein will contain, per unit dosage, e.g., tablet, capsule, powder, injection, teaspoonful, suppository and the like. The compositions will be administered in amounts as previously described herein with regard to the active ingredient and to the condition being treated. The dosages, however, may be varied depending upon the requirement of the patient, the severity of the condition being treated, and the compound being employed. Determination of optimum dosages for a particular situation is within the skill of the art.

In the following Examples and throughout the specification the following terms and abbreviations are used: g (grams); mL (milliliters); L (liters); min (minutes); hr (hours); mol (moles); v/v (volume to volume); DMF (N,N-dimethylformamide); Et$_2$O (diethyl ethyl); EtOAc (ethyl acetate); NBS (N-bromosuccinimide); THF (tetrahydrofuran); RT (room temperature); C, H, N, etc. (the chemical symbols for the elements); Calcd. (calculated); $[\alpha]_D^{25}$ (specific rotation measured at 25° C. with 589 nanometer light); c (concentration in grams per 100 mL); mp (melting point); decomp. (decomposition); TLC (thin layer chromatography); and Celite ® (filter agent). All melting points are corrected.

EXAMPLE 1

2,3-O-(1-Methylethylidene)-4,5-O-sulfonyl-$\beta$-D-fructopyranose Sulfamate.

A 3 L three-necked flask was equipped with a mechanical stirrer, thermometer, addition funnel, and an argon inlet. 2,3-O-(1-Methylethylidene)-$\beta$-D-fructopyranose 1-sulfamate (50.0 g, 0.167 mol) was combined with EtOAc (1.7 L) and pyridine (31.7 g, 0.401 mol). This mixture was heated at reflux while stirring under argon to effect solution and cooled to −60° C. with a dry ice/isopropanol bath. Sulfuryl chloride (49.6 g, 0.370 mol) was added dropwise over 45 min at −60° to −50° C. while stirring under argon. The resulting white slurry was stirred at −60° to −50° C. for 1 hr, then at RT for 2 hr, and filtered through Celite ®. The filtrate was extracted sequentially with saturated aqueous NaCl, 1N HCl, saturated aqueous NaHCO$_3$ (twice), saturated aqueous NaCl, dried over anhydrous MgSO$_4$, filtered through Celite ® and concentrated in vacuo at 40° C. to furnish 85.6 g (100%) of 4,5-bis-O-chlorosulfonyl-2,3-O-(1-methylethylidene)-$\beta$-D-fructopyranose sulfamate as a white crystalline solid, which was used without further purification. An analytical sample was purified by column chromatography on silica gel eluting with CH$_2$Cl$_2$/EtOAc (95:5 v/v); mp 119°-121° C. (decomp.).

A solution of 4,5-bis-O-chlorosulfonyl-2,3-O-(1-methylethylidene)-$\beta$-D-fructopyranose sulfamate (83.1 g, 0.167 mol) in 418 mL of methanol was combined with NaHCO$_3$ (84.2 g, 1.00 mol) at RT in a 2 L three-necked flask equipped with a mechanical stirrer and an argon inlet. This mixture was stirred at RT under argon for 18 hr, filtered through Celite ® and concentrated in vacuo at 40° C. The residue was dissolved in EtOAc and extracted twice with saturated aqueous NaCl, dried over anhydrous MgSO$_4$, filtered through Celite ® and concentrated in vacuo at 40° C. to afford 59.3 g (98%) of product as an oil which crystallized on standing. This material was purified by column chromatography on silica gel eluting with CH$_2$Cl$_2$/EtOAc (9:1 v/v) to furnish 36.6 g (53%) of product. The isolated product (36.6 g) was dissolved in anhydrous ethanol (total volume=150 mL), filtered through Celite ®, diluted to 350 mL with water, seeded and allowed to recrystallize at 5° C. The resulting white crystals were washed with a cold mixture of ethanol/water (1:1), then with water and dried in vacuo at 40° C. (18 h) to give 31.4 g of pure 2,3-O-(1-methylethylidene)-O-4,5-sulfonyl-$\beta$-D-fructopyranose sulfamate, mp 139°-141° C. (decomp.); $[\alpha]_D^{25}=-28.8°$ (c=1.17, CH$_3$OH). Anal. Calcd. for C$_9$H$_{15}$NO$_{10}$S$_2$:C, 29.92; H, 4.18; N, 3.88. Found: C, 30.01; H, 4.36; N, 3.80.

EXAMPLE 2

2,3-O-(1-Methylethylidene)-4,5-O-sulfonyl-$\beta$-L-fructopyranose Sulfamate 2,3-O-(1-Methylethylidene)-$\beta$-L-fructopyranose 1-sulfamate was prepared from L-fructose using the same procedure described for the D-isomer (J. Med. Chem. 1987, 30, 880) mp=124°-127° C. (decomp.); $[\alpha]_D^{25}=-26.4°$ (c=0.83, CH$_3$OH). The 2,3-O-(1-methylethylidene)-$\beta$-L-fructopyranose 1-sulfamate thus obtained was converted to the title compound using the procedure described above for Example 1 (i.e. the D-isomer) to provide 1.19 g of 2,3-O-(1-methylethylidene)-4,5-O-sulfonyl-$\beta$-L-fructopyranose sulfamate, mp 128°-129° C. (decomp.); $[\alpha]_D^{25}=+27.1°$ (c=1.18, CH$_3$OH). Anal. Calcd. for C$_9$H$_{15}$NO$_{10}$S$_2$:C, 29.92; H, 4.18; N, 3.88; S, 17.75. Found: C, 30.07; H, 4.18N, 3.83; S, 17.62.

EXAMPLE 3

2,3-O-(1-Methylethylidene)-4,5-O-sulfonyl-$\beta$-D-fructopyranose Methylsulfamate.

A 1 L three-necked flask containing a solution of sulfuryl chloride (17.1 g, 0.127 mol) in 100 mL of dry toluene was equipped with a mechanical stirrer, thermometer, addition funnel, and an argon inlet and cooled to −60° C. A solution of 2,3-O-(1-methylethylidene)-4,5-O-sulfonyl-$\beta$-D-fructopyranose (29.8 g, 0.101 mol; Can. J. Chem. 1982, 60, 1857) and pyridine (10.0 g, 0.127 mol) in 422 mL of toluene was added dropwise to the sulfuryl chloride solution over 45 min at −55° to −60° C. while stirring vigorously under argon. After 2 hr at −55° to −60° C., the reaction was filtered through a pad of Celite ®. The filtrate was extracted sequentially with water, twice with 1N H$_2$SO$_4$, twice with saturated aqueous NaHCO$_3$, twice with saturated aqueous NaCl, dried over anhydrous MgSO$_4$, filtered through a pad of Celite ® and concentrated in vacuo to afford 31.9 g of crude chlorosulfate as a brown oil. This material was purified by column chromatography on silica gel eluting with CH$_2$Cl$_2$ to provide 28.9 g (72%) of 2,3-O-(1-methylethylidene)-4,5-O-sulfonyl-$\beta$-D-fructopyranose chlorosulfate as a white crystalline solid. An analytical sample was recrystallized from anhydrous ethanol; mp 93°-95° C.; $[\alpha]_D^{25} = -35.4°$ (c=0.86, CH$_3$OH). Anal. Calcd. for C$_9$H$_{13}$ClO$_{10}$S$_2$: C, 28.39; H, 3.44; Cl, 9.31; S, 16.84. Found: C, 28.53; H, 3.46; Cl, 9.17; S, 16.98.

The 2,3-O-(1-methylethylidene)-4,5-O-sulfonyl-β-D-fructopyranose chlorosulfate thus obtained (2.48 g, 0.0065 mol) was dissolved in 33 mL of THF and cooled to 5° C. while stirring under argon. Excess anhydrous methylamine was bubbled through the solution over 30 min while maintaining the temperature between 5° and 10° C. After 30 min, the reaction was filtered through a pad of Celite ®, concentrated in vacuo and the residue was chromatographed on silica gel eluting with hexane/EtOAc (85:15 v/v) to furnish 2.21 g (90%) of 2,3-O-(1-methylethylidene)-4,5-O-sulfonyl-β-D-fructopyranose methylsulfamate as clear hard glass; $[\alpha]_D^{25} = -25.3°$ (c=1.00, CH$_3$OH). Anal. Calcd. for C$_{10}$H$_{17}$NO$_{10}$S$_2$: C, 32.00; H, 4.56; N, 3.73. Found: C, 32.30; H, 4.54; N, 3.83.

EXAMPLE 4

2,3-O-(1-Methylethylidene)-4,5-O-sulfonyl-β-D-fructopyranose Butylsulfamate 2,3-O-(1-Methylethylidene)-4,5-O-sulfonyl-β-D-fructopyranose chlorosulfate (2.49 g, 0.0065 mol), prepared as described in Example 3, was dissolved in 33 mL of THF, cooled to 5° C. via an ice bath and treated with anhydrous n-butylamine (5.77 g, 0.0789 mol) while stirring under argon. Fifteen minutes after the addition, the ice bath was removed and the reaction was stirred at RT for 4 hr, concentrated in vacuo, and purified by column chromatography on silica gel eluting with hexane/EtOAc (7:3 v/v) and recrystallized from ethanol/water (3:1 v/v) to provide 2.01 g (74%) of 2,3-O-(1-methylethylidene)-4,5-O-sulfonyl-β-D-fructopyranose butylsulfamate as a white crystalline solid; mp 111°-113° C.; $[\alpha]_D^{25} = -25.1°$ (c=1.00, CH$_3$OH). Anal. Calcd. for C$_{13}$H$_{23}$NO$_{10}$S$_2$: C, 37.40; H, 5.55; N, 3.36 Found: C, 37.87; H, 5.65; N, 3.30.

EXAMPLE 5

2,3-O-(1-Methylethylidene)-4,5-O-sulfonyl-β-D-fructopyranose Ethylsulfamate

Excess anhydrous ethylamine was reacted with 2,3-O-(1-methylethylidene)-4,5-O-sulfonyl-β-D-fructopyranose chlorosulfate (2.54 g, 0.0066 mol) in the same manner as described in Example 3 and chromatographed on silica gel eluting with hexane/EtOAc (4:1 v/v) to provide 2.30 g (89%) of 2,3-O-(1-methylethylidene)-4,5-O-sulfonyl-β-D-fructopyranose ethylsulfamate as a hard glass; $[\alpha]_D^{25} = -23.6°$ (c=1.00, CH$_3$OH). Anal. Calcd. for C$_{11}$H$_{19}$NO$_{10}$S$_2$. 0.2 EtOAc: C, 34.82; H, 5.10; N, 3.44. Found: C, 35.04; H, 4.84; N, 3.13.

EXAMPLE 6

2,3-O-(1-Methylethylidene)-4,5-O-sulfonyl-β-D-fructopyranose Octylsulfamate

Excess anhydrous octylamine (2.46 mL, 0.0148 mol) was reacted with 2,3-O-(1-methylethylidene)-4,5-O-sulfonyl-β-D-fructopyranose chlorosulfate (1.88 g, 0.0049 mol) in the same manner as described in Example 4 and chromatographed on silica gel eluting with CH$_2$Cl$_2$/EtOAc (4:1 v/v) to provide 1.11 g (48%) of 2,3-O-(1-methylethylidene)-4,5-O-sulfonyl-β-D-fructopyranose octylsulfamate as an oil; $[\alpha]_D^{25} = -17.1°$ (c=1.00, CH$_3$OH). Anal. Calcd. for C$_{17}$H$_{31}$NO$_{10}$S$_2$.0.1 EtOAc: C, 43.33; H, 6.64; N, 2.90; S, 13.29 Found: C, 43.64; H, 6.68; N, 3.02; S, 13.06.

EXAMPLE 7

2,3-O-(1-Methylethylidene)-4,5-O-sulfonyl-β-D-fructopyranose 2-Propenylsulfamate Excess anhydrous allylamine (1.35 g, 0.0236 mol) was reacted with 2,3-O-1-methylethylidene)-4,5-O-sulfonyl-β-D-fructopyranose chlorosulfate (3.00 g, 0.0079 mol) in the same manner as described in Example 4, filtered through a pad of Celite ®, concentrated in vacuo, and dissolved in EtOAc. The EtOAc solution was extracted twice with 1N HCl, saturated aqueous NaHCO$_3$, and saturated aqueous NaCl and then dried over anhydrous MgSO$_4$. The EtOAc was removed in vacuo and the residue was purified by column chromatography on silica gel eluting with hexane/EtOAc (7:3 v/v) and recrystallized from ethanol/water (1:1 v/v) to provide 1.75 g (55%) of 2,3-O-(1-methylethylidene)-4,5-O-sulfonyl-β-D-fructopyranose 2-propenylsulfamate as a white crystalline solid; mp 75°-77° C.; $[\alpha]_D^{25} = -31.1°$ (c=1.00, CH$_3$OH). Anal. Calcd. for C$_{12}$H$_{19}$NO$_{10}$S$_2$: C, 35.91 H, 4.77; N, 3.49; S, 15.97 Found: C, 35.98; H, 4.75; N, 3.49; S, 16.05.

EXAMPLE 8

2,3-O-(1-Methylethylidene)-4,5-O-sulfonyl-β-D-fructopyranose Phenylmethylsulfamate Excess anhydrous benzylamine (1.69 g, 0.0158 mol) was reacted with 2,3-O-(1-methylethylidene)-4,5-O-sulfonyl-β-D-fructopyranose chlorosulfate (2.00 g, 0.0053 mol) in the same manner as described in Example 4 and purified by column chromatography on silica gel eluting with hexane/EtOAc (7:3 v/v) to provide 1.73 g (72%) of 2,3-O-(1-methylethylidene)-4,5-O-sulfonyl-β-D-fructopyranose phenylmethylsulfamate as a white foam; $[\alpha]_D^{25} = -22.8°$ (c=1.00, CH$_3$OH). Anal. Calcd. for C$_{16}$H$_{21}$NO$_{10}$S$_2$: C, 42.57; H, 4.69; N, 3.10; S, 14.20. Found: C, 42.77; H, 4.68; N, 3.15; S, 14.26.

EXAMPLE 9

2,3-O-(1-Methylethylidene)-4,5-O-sulfonyl-β-D-fructopyranose Cyclopropylsulfamate Excess anhydrous cyclopropylamine (0.90 g, 0.0172 mol) was reacted with 2,3-O-(1-methylethylidene)-4,5-O-sulfonyl-β-D-fructopyranose chlorosulfate (2.00 g, 0.0053 mol) in the same manner as described in Example 4 to give 0.95 g (45%) of 2,3-O-(1-methylethylidene)-4,5-O-sulfonyl-β-D-fructopyranose cyclopropylsulfamate as a white foam after chromatography on silica gel eluting with hexane/EtOAc (4:1 v/v); $[\alpha]_D^{25} = -24.8°$ (c=1.00, CH$_3$OH). Anal. Calcd. for C$_{12}$H$_{19}$NO$_{10}$S$_2$: C, 35.91 H, 4.77; N, 3.49; S, 15.97 Found: C, 36.16; H, 4.83; N, 3.43; S, 15.81.

EXAMPLE 10

2,3-O-(1-Methylethylidene)-4,5-O-sulfonyl-β-D-fructopyranose Cyclobutylsulfamate Excess anhydrous cyclobutylamine (1.12 g, 0.0158 mol) was reacted with 2,3-O-(1-methylethylidene)-4,5-O-sulfonyl-β-D-fructopyranose chlorosulfate (2.00 g, 0.0053 mol) in the same manner as described in Example 4 to give 1.89 g (87%) of 2,3-O-(1-methylethylidene)-4,5-O-sulfonyl-β-D-fructopyranose cyclobutylsulfamate as a white foam after chromatography on silica gel eluting with hexane/EtOAc (4:1 v/v); $[\alpha]_D^{25} = -29.2°$ (c=1.00, CH$_3$OH). Anal. Calcd. for C$_{13}$H$_{21}$NO$_{10}$S$_2$: C, 37.59; H, 5.10; N, 3.37; S, 15.43 Found: C, 37.48; H, 5.06; N, 3.35; S, 15.38.

EXAMPLE 11

2,3-O-(1-Methylethylidene)-4,5-O-sulfonyl-$\beta$-D-fructopyranose Cyclooctylsulfamate Excess anhydrous cyclooctylamine (3.01 g, 0.0236 mol) was reacted with 2,3-O-(1-methylethylidene)-4,5-O-sulfonyl-$\beta$-D-fructopyranose chlorosulfate (3.00 g, 0.0079 mol) in the same manner as described in Example 4 to give 2.10 g (57%) of 2,3-O-(1-methylethylidene)-4,5-O-sulfonyl-$\beta$-D-fructopyranose cyclooctylsulfamate as a white foam after chromatography on silica gel eluting with hexane/EtOAc (7:3 v/v); $[\alpha]_D^{25} = -23.5°$ (c=1.00, CH$_3$OH). Anal. Calcd. for C$_{17}$H$_{29}$NO$_{10}$S$_2$: C, 43.40; H, 6.00; N, 2.98; S, 13.63. Found: C, 43.40; H, 6.13; N, 3.01; S, 13.72.

EXAMPLE 12

2,3-O-(1-Methylethylidene)-4,5-O-sulfonyl-$\beta$-D-fructopyranose (2,2,2-Trifluoroethyl)sulfamate Excess anhydrous 2,2,2-trifluoroethylamine (3.12 g, 0.0315 mol) was reacted with 2,3-O-(1-methylethylidene)-4,5-O-sulfonyl-$\beta$-D-fructopyranose chlorosulfate (2.00 g, 0.0053 mol) in the same manner as described for Example 4 to give 1.83 g (79%) of 2,3-O-(1-methylethylidene)-4,5-O-sulfonyl-$\beta$-D-fructopyranose (2,2,2-trifluoroethyl)sulfamate as a clear crystalline solid after chromatography on silica gel eluting with hexane/EtOAc (7:3 v/v); mp 125°-127° C.; $[\alpha]_D^{25} = -24.3°$ (c=1.00, CH$_3$OH). Anal. Calcd. for C$_{11}$H$_{16}$F$_3$NO$_{10}$S$_2$: C, 29.80; H, 3.64; N, 3.16; S, 14.40. Found: C, 30.04; H, 3.52; N, 3.10; S, 14.01.

EXAMPLE 13

2,3-O-(1-Methylethylidene)-4,5-O-sulfonyl-$\beta$-D-fructopyranose Dimethylsulfamate Sodium hydride (60% oil dispersion; 0.73 g, 0.0183 mol) was extracted three times with anhydrous Et$_2$O while under argon, suspended in 40 mL of dry THF and cooled to 5° C. 2,3-O-(1-Methylethylidene)-O-4,5-sulfonyl-$\beta$-D-fructopyranose sulfamate (i.e. Example 1; 3.00 g, 0.0083 mol) was added as a solid portion-wise at 5° C. over 10 min while stirring under argon. After the hydrogen evolution ceased, excess iodomethane (5.16 mL, 0.083 mol) was added. The reaction mixture was heated to reflux for 1 hour, concentrated in vacuo, acidified with ca. 20 mL of 1N HCl, diluted with saturated aqueous NaCl and extracted three times with EtOAc. The combined EtOAc extracts were extracted twice with aqueous 0.1N Na$_2$S$_2$O$_3$, twice with saturated aqueous NaHCO$_3$, twice with saturated aqueous NaCl, dried over anhydrous MgSO$_4$, filtered through Celite ® and concentrated in vacuo to furnish 2.10 g of crude product. This material was recrystallized from 50 mL of EtOH/H$_2$O (2:3) to provide 1.78 g (55%) of 2,3-O-(1-methylethylidene)-4,5-O-sulfonyl-$\beta$-D-fructopyranose dimethylsulfamate; mp 109°-111° C.; $[\alpha]_D^{25} = -25.3°$ (c=1.00, CH$_3$OH). Anal. Calcd. for C$_{11}$H$_{19}$NO$_{10}$S$_2$: C, 33.93; H, 4.92; N, 3.60; S, 16.47. Found: C, 34.20; H, 4.87; N, 3.55; S, 16.55.

EXAMPLE 14

2,3-O-(1-Methylethylidene)-4,5-O-sulfonyl-$\beta$-D-fructopyranose Diethylsulfamate Excess anhydrous N,N-diethylamine (1.73 g, 0.0236 mol) was reacted with 2,3-O-(1-methylethylidene)-4,5-O-sulfonyl-$\beta$-D-fructopyranose chlorosulfate (3.00 g, 0.0079 mol) in the same manner as described in Example 4 to give 1.55 g (47%) of 2,3-O-(1-methylethylidene)-4,5-O-sulfonyl-$\beta$-D-fructopyranose diethylsulfamate as a white foam after chromatography on silica gel eluting with hexane/EtOAc (7:3 v/v); $[\alpha]_D^{25} = -26.3°$ (c=1.00, CH$_3$OH). Anal. Calcd. for C$_{13}$H$_{23}$NO$_{10}$S$_2$: C, 37.40; H, 5.55; N, 3.36; S, 15.36. Found: C, 37.39; H, 5.55; N, 3.33; S, 15.41.

EXAMPLE 15

2,3-O-(1-Methylethylidene)-4,5-O-sulfonyl-$\beta$-D-fructopyranose Azidosulfate

O-(1-Methylethylidene)-4,5-O-sulfonyl-$\beta$-D-fructopyranose chlorosulfate (2.00 g, 0.0053 mol), prepared as described in Example 3, was combined with anhydrous pyridine (0.83 g, 0.0105 mol) in 26 mL of anhydrous acetonitrile while stirring under argon. Sodium azide (0.68 g, 0.0105 mol) was added and the reaction mixture was stirred under argon at RT for 18 hours. The crude reaction mixture was filtered through Celite ®, concentrated in vacuo, and purified by chromatography on silica gel eluting with hexane/EtOAc (4:1 v/v) to provide 1.76 g (87%) of 2,3-O-(1-methylethylidene)-4,5-O-sulfonyl-$\beta$-D-fructopyranose azidosulfate as a clear glass; $[\alpha]_D^{25} = -21.0°$ (c=1.00, CH$_3$OH). Anal. Calcd. for C$_9$H$_{13}$N$_3$O$_{10}$S$_2$: C, 28.76; H, 3.58; N, 10.68; S, 16.30. Found: C, 28.77; H, 3.70; N, 10.29; S, 15.84.

EXAMPLE 16

(S)-2,3-O-(1-Methylethylidene)-4,5-O-sulfinyl-$\beta$-D-fructopyranose Sulfamate 2,3-O-(1-Methylethylidene)-1-O-phenylmethyl-$\beta$-D-fructopyranose (6.00 g, 0.0193 mol) was dissolved in 75 mL of anhydrous dioxane and heated to reflux while stirring under argon. Thionyl chloride (28 mL, 0.384 mol) was added dropwise over 10 min to the refluxing solution. After 15 min, the reaction mixture was cooled to RT and concentrated in vacuo. The residue was dissolved in EtOAc and extracted twice with saturated aqueous NaHCO$_3$, twice with saturated aqueous NaCl, dried over anhydrous MgSO$_4$, filtered through Celite ®, and concentrated in vacuo to yield 6.50 g (95%) of a 2.1:1 diastereomeric mixture of the (S) and (R) isomers of 2,3-O-(1-methylethylidene)-1-O-phenylmethyl-4,5-O-sulfinyl-$\beta$-D-fructopyranose. The individual (S) and (R) diastereomers were isolated in isomerically pure form by chromatography on silica gel eluting with hexane/EtOAc (9:1 v/v). The fractions containing the faster eluting (S)-isomer were combined and concentrated in vacuo to give 4.05 g of (S)-2,3-O-(1-methylethylidene)-1-O-phenylmethyl-4,5-O-sulfinyl-$\beta$-D-fructopyranose as a white crystalline solid; mp 92°-94° C. Similarly, the fractions containing the R-isomer were combined and concentrated in vacuo to give 1.93 g of (R)-2,3-O-(1-methylethylidene)-1-O-phenylmethyl-4,5-O-sulfinyl-$\beta$-D-fructopyranose as a clear oil.

The (S)-2,3-O-(1-methylethylidene)-1-O-phenylmethyl-4,5-O-sulfinyl-$\beta$-D-fructopyranose thus obtained (3.99 g, 0.112 mol) was dissolved in 560 mL of CH$_2$Cl$_2$ that had been previously saturated with water. N-Bromosuccinimide (1.99 g, 0.0112 mol) was added and the resulting solution was degassed with nitrogen over 60 min. The solution was cooled to 5° C. and the reaction was irradiated with a 150 watt incandescent flood light for 15 min. quenched with excess cyclohexene (7 mL) and basified with triethylamine (1.56 mL). The reaction was concentrated in vacuo, partially dissolved in 200 mL of EtOAc and filtered through Celite®. The filtrate was concentrated in vacuo and the residue was purified by column chromatography on silica gel eluting with hexane/Et$_2$O (3:2 v/v) to give 2.43 g (81%) of (S)-2,3-O-(1-methylethylidene)-4,5-O-sulfinyl-$\beta$-D-fructopyranose as a clear oil.

The (S)-2,3-O-(1-methylethylidene)-4,5-O-sulfinyl-$\beta$-D-fructopyranose (2.29 g, 0.0086 mol) thus obtained and triethylamine (14 mL) were dissolved in anhydrous EtOAc (86 mL) and cooled to $-60°$ C. while stirring under argon. Sulfamoyl chloride (6.45 g, 0.0558 mol) was added a solid in one portion and the reaction was allowed to slowly warm to RT over 18 hr. The reaction was extracted twice with 3N HCl, twice with saturated aqueous NaHCO$_3$, twice with saturated NaCl, dried over anhydrous MgSO$_4$, filtered through Celite® and concentrated in vacuo to give 2.43 g of crude product as a tan solid. This material was recrystallized from 5 mL of anhydrous ethanol to provide 1.20 g (40%) of (S)-2,3-O-(1-methylethylidene)-4,5-O-sulfinyl-$\beta$-D-fructopyranose sulfamate as a white crystalline solid; mp 151.5°–153.5° C.; $[\alpha]_D^{25} = -14.9°$ (c=1.00, CH$_3$OH). Anal. Calcd. for C$_9$H$_{15}$NO$_9$S$_2$: C, 31.30; H, 4.38; N, 4.06; S, 18.57. Found: C, 31.48; H, 4.39; N, 4.08; S, 18.46.

EXAMPLE 17

(R)-2,3-O-(1-Methylethylidene)-4,5-O-sulfinyl-$\beta$-D-fructopyranose Sulfamate The (R)-2,3-O-(1-methylethylidene)-1-O-phenylmethyl-4,5-O-sulfinyl-$\beta$-D-fructopyranose (4.33 g, 0.0122 mol) that was prepared and isolated as described in Example 16 was oxidatively debenzylated with N-bromosuccinimide (2.17 g, 0.0122 mol) in the same manner described for Example 16, i.e. the (S)-isomer, to provide 1.09 g (34%) of (R)-2,3-O-(1-methylethylidene)-4,5-O-sulfinyl-$\beta$-D-fructopyranose as a clear oil. Similarly, this material was reacted with sulfamoyl chloride (2.86 g, 0.0248 mol) and recrystallized from ethanol in the same manner described in Example 16 to furnish 0.25 g of (R)-2,3-O-(1-methylethylidene)-4,5-O-sulfinyl-$\beta$-D-fructopyranose sulfamate as a white crystalline solid; mp 197°–199° C., decomp; $[\alpha]_D^{25} = -43.5°$ (c=1.00, CH$_3$OH). Anal. Calcd. for C$_9$H$_{15}$NO$_9$S$_2$: C, 31.30; H, 4.38; N, 4.06; S, 18.57. Found: C, 31.55; H, 4.41; N, 4.10; S, 18.33.

EXAMPLE 18

2,3-O-(1-Ethylpropylidene)-4,5-O-sulfonyl-$\beta$-D-fructopyranose Sulfamate

D-fructose (100.0 g, 0.555 mol) was suspended in 3-pentanone (2.3 L, 1.127 mol) and heated to 40° C. and concd H$_2$SO$_4$ (60 mL) was added dropwise over 20 min. Twenty-five minutes after the addition, the reaction was cooled from 40° C. to 5° C., cautiously basified to pH 11 with 3N aqueous NaOH and concentrated in vacuo. The residue was diluted with water and extracted 3 times with CH$_2$Cl$_2$. The combined CH$_2$Cl$_2$ extracts were washed twice with water, dried over anhydrous Na$_2$SO$_4$, filtered through Celite® and concentrated in vacuo to give 18.5 g (11%) of product as a brown oil, which was purified by column chromatography on silica gel eluting with hexane/EtOAc (6:1 v/v) to give 2,3:4,5-bis-O-(1-ethylpropylidene)-$\beta$-D-fructopyranose as a white crystalline solid; mp 46°–48° C.; $[\alpha]_D^{25} = -36.6°$ (c=1.00, CH$_3$OH). Anal. Calcd. for C$_{16}$H$_{28}$O$_6$: C, 60.74; H, 8.92. Found: C, 60.77; H, 8.93.

2,3:4,5-Bis-O-(1-Ethylpropylidene)-$\beta$-D-fructopyranose (17.19 g, 0.0541 mol) was combined with pyridine (5.13 g, 0.0649 mol) and dissolved in 73 mL of dry toluene. This solution was added dropwise over 15 min at $-20°$ C. to a vigorously stirred solution of sulfuryl chloride (8.75 g, 0.0649 mol) in 75 mL of dry toluene. After the addition, the reaction was allowed to slowly warm to RT over 3 hr, and diluted with water. The toluene layer was extracted 3 times with 10% aqueous citric acid, three times with saturated aqueous NaHCO$_3$, twice with saturated aqueous NaCl, dried over anhydrous Na$_2$SO$_4$, filtered through Celite® and concentrated in vacuo to afford 25.4 g of crude 2,3:4,5-bis-O-(1-ethylpropylidene)-$\beta$-D-fructopyranose chlorosulfate. This crude chlorosulfate was dissolved in dry THF (300 mL) and placed in a vigorously stirred autoclave under 30 psig of anhydrous ammonia over 18 hr. The reaction was filtered through Celite® and concentrated in vacuo. The residue was purified by column chromatography on silica gel eluting with hexane/EtOAc (3:1 v/v) to give 2,3:4,5-bis-O-(1-ethylpropylidene)-$\beta$-D-fructopyranose sulfamate as a clear syrup; $[\alpha]_D^{25} = -19.7°$ (c=1.00, CH$_3$OH). Anal. Calcd. for C$_{16}$H$_{29}$NO$_8$S: C, 48.59; H, 7.39; N, 3.54; S, 8.11. Found: C, 48.36; H, 7.41; N, 3.51; S, 8.11.

2,3:4,5-Bis-O-(1-Ethylpropylidene)-$\beta$-D-fructopyranose sulfamate (14.56 g, 0.0368 mol) was dissolved in THF (362 mL), heated to 43° C. and acidified with 184 mL of 6N aqueous HCl while stirring vigorously. After 1 hr, the reaction was cooled to 5° C., the pH was adjusted to pH 7 with Na$_2$CO$_3$ and the aqueous layer was saturated with NaCl. The resulting layers were separated and the aqueous layer was extracted 2 more times with THF. The combined THF extracts were dried over anhydrous MgSO$_4$, filtered through Celite® and concentrated in vacuo. The residue was purified by column chromatography on silica gel eluting with EtOAc/CH$_2$Cl$_2$ (3:2 v/v) to give 2.53 g (21%) of 2,3-O-(1-ethylpropylidene)-$\beta$-D-fructopyranose 1-sulfamate as a clear syrup; $[\alpha]_D^{25} = +22.7°$ (c=1.00, CH$_3$OH). Anal. Calcd. for C$_{11}$H$_{21}$NO$_8$S: C, 40.36; H, 6.47; N, 4.28; S, 9.79. Found: C, 40.46; H, 6.50; N, 4.12; S, 9.66.

2,3-O-(1-Ethylpropylidene)-$\beta$-D-fructopyranose 1-sulfamate (1.82 g, 0.0056 mol) and pyridine (1.06 mL, 0.0134 mol) were dissolved in EtOAc (55 mL) and reacted with sulfuryl chloride (1.65 g, 0.0122 mol) as described for Example 1 to provide the corresponding bis-chlorosulfate. Analogous dechlorosulfation of this bis-chlorosulfate with NaHCO$_3$ (2.67 g, 0.0318 mol) in methanol (16 mL) followed by purification by preparative TLC on silica gel eluting with Et$_2$O/hexane (7:3 v/v) provided 0.79 g of 2,3-O-(1-ethylpropylidene)-4,5-O-sulfonyl-$\beta$-D-fructopyranose sulfamate as a white crystalline solid; mp 130°–133° C.; $[\alpha]_D^{25} = -23.1°$ (c=1.17, CH$_3$OH). Anal. Calcd. for C$_{11}$H$_{19}$NO$_{10}$S$_2$: C, 33.93; H, 4.92; N, 3.60; S, 16.47. Found: C, 34.21; H, 4.95; N, 3.54; S, 16.29.

EXAMPLE 19

2,3-O-(1-Methylethylidene)-4,5-O-[N-(4-methylbenzenesulfonyl)imidosulfinyl]-β-D-fructopyranose Sulfamate To a solution of 2,3-O-(1-methylethylidene)-β-D-fructopyranose 1-sulfamate (10.0 g, 0.0334 mol) in 120 mL of dry THF was added a solution of crude N-(p-toluenesulfonyl)imidothionyl chloride (34.1 g, 0.1254 mol) in 120 mL of dry benzene dropwise at 5° C. over 15 min while stirring vigorously under argon. The reaction was allowed to slowly warm to RT over 2 hr and was subsequently concentrated in vacuo. The residue was cautiously quenched with saturated aqueous NaHCO$_3$ and extracted with EtOAc. The basic aqueous layer was extracted two more times with EtOAc, and the combined EtOAc extracts were extracted with saturated aqueous NaHCO$_3$, twice with saturated aqueous NaCl, dried over anhydrous MgSO$_4$, filtered through Celite ® and concentrated in vacuo. The residue was dissolved in 200 mL of boiling CH$_2$Cl$_2$/EtOAc (19:1 v/v) and p-toluenesulfonamide precipitated from the solution on cooling to RT. The p-toluenesulfonamide was isolated by filtration and the filtrate was purified by column chromatography on silica gel eluting with CH$_2$Cl$_2$/EtOAc (19:1 v/v) to give 9.35 g (56%) of 2,3-O-(1-methylethylidene)-4,5-O-[N-(4-methylbenzenesulfonyl)imidosulfinyl]-β-fructopyranose sulfamate as a white foam; mp 68°–73° C.; $[\alpha]_D^{25} = +23.3°$ (c=1.00, CH$_3$OH). Anal. Calcd. for C$_{16}$H$_{22}$N$_2$O$_{10}$S$_3$: C, 38.55; H, 4.45; N, 5.64; S, 19.29. Found: C, 38.52; H, 4.57; N, 5.38; S, 19.07.

EXAMPLE 20

2,3-O-(1-Methylethylidene)-4,5-O-[N-(4-methylbenzenesulfonyl)imidosulfonyl]-β-D-fructopyranose Sulfamate 2,3-O-(1-Methylethylidene)-4,5-O-[N-(4-methylbenzenesulfonyl) imidosulfinyl]-β-D-fructopyranose sulfamate (3.10 g, 0.0062 mol) was dissolved in 19 mL of CH$_3$CN and diluted with 19 mL of CCl$_4$. Water (28 mL) was added and this mixture was cooled to 5° C. while stirring vigorously with a mechanical stirrer. Sodium periodate (2.92 g, 0.0136 mol) was added followed by a catalytic amount of RuCl$_3$.H$_2$O (0.0300 g, 0.00015 mol). The reaction was allowed to warm to RT over 20 hr and diluted with 150 mL of EtOAc. The layers were separated and the aqueous layer was extracted two more times with EtOAc. The combined EtOAc extracts were washed twice with saturated aqueous NaCl, dried over anhydrous MgSO$_4$, filtered through Celite ® and concentrated in vacuo. The residue was purified by column chromatography on silica gel eluting with Et$_2$O/hexane (4:1 v/v), dissolved in CH$_2$Cl$_2$, filtered through Celite ® and concentrated in vacuo to give 0.72 g (23%) of 2,3-O-(1-methylethylidene)-4,5-O-[N-(4-methylbenzenesulfonyl)imidosulfonyl]-β-D-fructopyranose sulfamate as a solvate with CH$_2$Cl$_2$ and n-hexane that appears as a hard white foam; mp 77°–101° C.; $[\alpha]_D^{25} = +4.1°$ (c=1.00, CH$_3$OH). Anal. Calcd. for C$_{16}$H$_{22}$N$_2$O$_{11}$S$_3$.0.2 CH$_2$Cl$_2$.0.1 C$_6$H$_{14}$: C, 37.32; H, 4.43; N, 5.20; S, 17.86. Found: C, 37.64; H, 4.48; N, 5.11; S, 17.76.

EXAMPLE 21

2,3-O-(Cyclohexylidene)-4,5-O-sulfonyl-β-D-fructopyranose Sulfamate 2,3:4,5-Bis-O-(Cyclohexylidene)-β-D-fructopyranose (22.6 g, 0.0664 mol; U.S. Pat. No. 4,659,809) was combined with pyridine (6.30 g, 0.0797 mol) and dissolved in 150 mL of dry toluene. This solution was added dropwise over 20 min at −20° C. to a vigorously stirred solution of sulfuryl chloride (8.75 g, 0.0649 mol) in 150 mL of dry toluene. After the addition, the reaction was allowed to slowly warm to RT over 4 hr, and diluted with water. The toluene layer was extracted 3 times with 10% aqueous citric acid, three times with saturated aqueous NaHCO$_3$, twice with saturated aqueous NaCl, dried over anhydrous MgSO$_4$, filtered through Celite ® and concentrated in vacuo to afford 33.1 g of crude 2,3:4,5-bis-O-(cyclohexylidene)-β-D-fructopyranose chlorosulfate. This crude chlorosulfate was dissolved in 132 mL of dry THF and placed in a vigorously stirred autoclave under 30 psig o anhydrous ammonia over 18 hr. The reaction was filtered through Celite ® and concentrated in vacuo. The residue was purified by column chromatography on silica gel eluting with hexane/EtOAc (7:3 v/v) to give 2,3:4,5-bis-O-(cyclohexylidene)-β-D-fructopyranose sulfamate as a hard white foam; $[\alpha]_D^{25} = -31.7°$ (c=1.00, CH$_3$OH). Anal. Calcd. for C$_{18}$H$_{29}$NO$_8$S.0.14 EtOAc: C, 51.62; H, 7.03; N, 3.24; S, 7.42. Found: C, 51.58; H, 7.02; N, 3.30; S, 7.70.

2,3:4,5-Bis-O-(Cyclohexylidene)-β-D-fructopyranose sulfamate (20.37 g, 0.0486 mol) was dissolved in THF (408 mL), acidified with 204 mL of 6N aqueous HCl and heated at 47°–50° C. for 5 hr while stirring vigorously. The reaction was cooled to 5° C., the pH was cautiously adjusted to pH 7 with Na$_2$CO$_3$ and the aqueous layer was saturated with NaCl. The resulting layers were separated and the aqueous layer was extracted 3 more times with THF. The combined THF extracts were dried over anhydrous MgSO$_4$, filtered through Celite ® and concentrated in vacuo. The residue was purified by column chromatography on silica gel eluting with EtOAc/CH$_2$Cl$_2$ (3:2 v/v) to give 2.85 g (17%) of 2,3-O-(cyclohexylidene)-β-D-fructopyranose 1-sulfamate as a white foam.

2,3-O-(Cyclohexylidene)-β-D-fructopyranose 1-sulfamate (2.33 g, 0.0069 mol) was combined with pyridine (1.22 mL, 0.0151 mol), dissolved in EtOAc (69 mL) and reacted with sulfuryl chloride (1.33 mL, 0.0165 mol) in the same manner as described for Example 1 to provide the corresponding bis-chlorosulfate. Analogous dechlorosulfation of this bis-chlorosulfate with NaHCO$_3$ (3.76 g, 0.0448 mol) in methanol (69 mL) followed by purification by column chromatography on silica gel with hexane/EtOAc (7:3 v/v) provided 1.42 g of product, which was recrystallized from 20 mL of EtOH/H$_2$O (1:1 v/v) to provide 1.21 g (44%) of 2,3-O-(cyclohexylidene)-4,5-O-sulfonyl-β-D-fructopyranose sulfamate as a white crystalline solid; mp 139°–141° C.; $[\alpha]_D^{25} = -31.5°$ (c=1.00, CH$_3$OH). Anal. Calcd. for C$_{12}$H$_{19}$NO$_{10}$S$_2$: C, 35.91; H, 4.77; N, 3.49; S, 15.97. Found: C, 36.08; H, 4.81; N, 3.45; S, 15.87.

EXAMPLE 22

(S)-4,5-O-[N-(1,1-Dimethylethoxycarbonyl)imidosulfinyl]-2,3-O-(1-methylethylidene)-β-D-fructopyranose Sulfamate.

N,N-Dichloro-t-butylcarbamate (10.0 g, 0.0537 mol) was combined with sulfur (1.72 g, 0.0537 mol) and tetrabutylammonium bromide (1.73 g, 0.0054 mol) in 50 mL of anhydrous benzene. The resulting suspension was heated at 40° C. for 2 hr while stirring vigorously under argon. After cooling to RT, the resulting solution of crude N-(t-butoxycarbonyl)imidothionyl chloride was transferred, while under argon, to an addition funnel and added dropwise at 5° C. over 15 min to a vigorously stirred solution of 2,3-O-(1-methylethylidene)-β-D-fructopyranose 1-sulfamate (5.19 g, 0.0173 mol) and anhydrous pyridine (4.60 mL, 0.0568 mol) in 173 mL of anhydrous THF. The reaction was stirred at 5° C. for 3 hr, filtered through Celite® and concentrated in vacuo. The crude residue was dissolved in EtOAc and extracted twice with saturated aqueous NaHCO$_3$, twice with saturated aqueous NaCl, dried over anhydrous MgSO$_4$, filtered through Celite® and concentrated in vacuo. The residue was purified by column chromatography on silica gel eluting with hexane/EtOAc (7:3 v/v) and recrystallized from 25 mL of anhydrous ethanol to yield 2.11 g (27%) of (S)-4,5-O-[N-(1,1dimethylethoxycarbonyl) imidosulfinyl]-2,3-O-(1-methylethylidene)-β-D-fructopyranose sulfamate as a white crystalline solid; mp 175°–176° C.; $[\alpha]_D^{25} = +19.5°$ (c=1.00, CH$_3$OH). Anal. Calcd. for C$_{14}$H$_{24}$N$_2$O$_{10}$S$_2$: C, 37.83; H, 5.44; N, 6.30; S, 14.43. Found: C, 38.05; H, 5.45; N, 6.36; S, 14.36.

We claim:

1. A compound of formula (I):

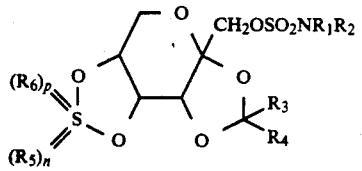

wherein R$_1$ and R$_2$ are the same or different and are hydrogen, C$_1$–C$_{12}$ alkyl, C$_3$–C$_{10}$ cycloalkyl, allyl, benzyl, CH$_2$(C$_1$–C$_4$ perfluoroalkyl), or are taken together with the N to represent an azido group;

wherein R$_3$ and R$_4$ are the same or different and are hydrogen, C$_1$–C$_6$ alkyl, or are taken together to form a cyclopentyl or cyclohexyl ring;

R$_5$ and R$_6$ may be the same or different and are oxygen or NR$_7$; wherein R$_7$ is selected from hydrogen, C$_1$–C$_4$ alkyl, C$_1$–C$_4$ perfluoroalkyl, arenesulfonyl, C$_1$–C$_4$ alkoxycarbonyl or benzyloxycarbonyl;

wherein n equals zero or one and p equals zero or one, provided that n and p are not both equal to zero at the same time;

and a pharmaceutically acceptable salt thereof.

2. The compound of claim 1, wherein said compounds are in the β-D-fructopyranose absolute configuration.

3. The compound of claim 1, wherein said compounds are in the β-L-fructopyranose absolute configuration.

4. The compound of claim 1, wherein R$_5$ and R$_6$ are oxygen.

5. The compound of claim 1, wherein n and p are equal to one.

6. The compound of claim 1, wherein R$_1$ and R$_2$ are hydrogen.

7. The compound of claim 1, wherein R$_1$ is hydrogen.

8. The compound of claim 1, wherein R$_3$ and R$_4$ are methyl.

9. The compound of claim 1, wherein R$_1$ and R$_2$ are hydrogen or methyl, R$_3$ and R$_4$ are each methyl, R$_5$ and R$_6$ are oxygen and n and p are equal to one.

10. The compounds of claim 1, wherein said compounds of formula (I) are selected from the group consisting of:

2,3-O-(1-methylethylidene)-4,5-O-sulfonyl-β-D-fructopyranose sulfamate;

2,3-O-(1-methylethylidene)-4,5-O-sulfonyl-β-L-fructopyranose sulfamate;

2,3-O-(1-methylethylidene)-4,5-O-sulfonyl-β-D-fructopyranose methylsulfamate;

2,3-O-(1-methylethylidene)-4,5-O-sulfonyl-β-D-fructopyranose butylsulfamate;

2,3-O-(1-methylethylidene)-4,5-O-sulfonyl-β-D-fructopyranose ethylsulfamate;

2,3-O-(1-methylethylidene)-4,5-O-sulfonyl-β-D-fructopyranose octylsulfamate;

2,3-O-(1-methylethylidene)-4,5-O-sulfonyl-β-D-fructopyranose 2-propenylsulfamate;

2,3-O-(1-methylethylidene)-4,5-O-sulfonyl-β-D-fructopyranose phenylmethylsulfamate;

2,3-O-(1-methylethylidene)-4,5-O-sulfonyl-β-D-fructopyranose cyclopropylsulfamate;

2,3-O-(1-methylethylidene)-4,5-O-sulfonyl-β-D-fructopyranose cyclobutylsulfamate;

2,3-O-(1-methylethylidene)-4,5-O-sulfonyl-β-D-fructopyranose cyclooctylsulfamate;

2,3-O-(1-methylethylidene)-4,5-O-sulfonyl-β-D-fructopyranose (2,2,2-trifluoroethyl)sulfamate;

2,3-O-(1-methylethylidene)-4,5-O-sulfonyl-β-D-fructopyranose dimethylsulfamate;

2,3-O-(1-methylethylidene)-4,5-O-sulfonyl-β-D-fructopyranose diethylsulfamate;

2,3-O-(1-methylethylidene)-4,5-O-sulfonyl-β-D-fructopyranose azidosulfate;

(S)-2,3-O-(1-methylethylidene)-4,5-O-sulfinyl-β-D-fructopyranose sulfamate;

(R)-2,3-O-(1-methylethylidene)-4,5-O-sulfinyl-β-D-fructopyranose sulfamate;

2,3-O-(1-ethylpropylidene)-4,5-O-sulfonyl-β-D-fructopyranose sulfamate;

2,3-O-(1-methylethylidene)-4,5-O-[N-(4-methylbenzenesulfonyl)imidosulfinyl]-β-D-fructopyranose sulfamate;

2,3-O-(1-methylethylidene)-4,5-O-[N-(4-methylbenzenesulfonyl)imidosulfonyl]-β-D-fructopyranose sulfamate;

2,3-O-(cyclohexylidene)-4,5-O-sulfonyl-β-D-fructopyranose sulfamate;

(S)-4,5-O-[N-(1,1-dimethylethoxycarbonyl)imidosulfinyl]-2,3-O-(1-methylethylidene)-β-D-fructopyranose sulfamate;

and the pharmaceutically acceptable salts thereof.

11. The compound of claim 10 wherein said compound is 2,3-O-(1-methylethylidene)-4,5-O-sulfonyl-β-D-fructopyranose sulfamate, and the pharmaceutically acceptable salts thereof.

12. A pharmaceutical composition effective for the treatment or prevention of convulsions comprising an amount effective for the prevention or treatment of convulsions of the compound of formula (I) as recited in claim 1 in admixture with a pharmaceutically acceptable carrier.

13. The pharmaceutical composition of claim 12, wherein said compound of formula (I) is present in a unit dosage amount of about 2.5 milligrams to about 500 milligrams.

14. A method for the prevention or treatment of convulsions in a mammal which comprises administering to the mammal a therapeutically effective amount of the compound of formula (I) as recited in claim 1.

15. A pharmaceutical composition effective for the treatment or prevention of peptic ulcers comprising an effective amount for the prevention or treatment of peptic ulcers of the compound of formula (I) as recited in claim 1 in admixture with a pharmaceutically acceptable carrier.

16. The pharmaceutical composition of claim 15, wherein said compound of formula (I) is present in a unit dosage amount of about 10 milligrams to about 1000 milligrams.

17. A method for the prevention or treatment of peptic ulcers in a mammal which comprises administering to the mammal a therapeutically effective amount of the compound of formula (I) as recited in claim 1.

18. A pharmaceutical composition effective for the treatment or prevention of glaucoma comprising an amount effective for the prevention or treatment of glaucoma of a compound of the formula (I) as recited in claim 1 in admixture with a pharmaceutically acceptable carrier.

19. The pharmaceutical composition of claim 18, wherein said compound of formula (I) is present in a unit dosage amount of about 0.1 milligrams to about 750 milligrams.

20. A method for the prevention or treatment of glaucoma in a mammal which comprises administering to the mammal a therapeutically effective amount of the compound of formula (I) as recited in claim 1.

21. A pharmaceutical composition effective for the treatment of hypertension comprising an amount effective for the treatment of hypertension of the compound of formula (I) as recited in claim 1 in admixture with a pharmaceutically acceptable carrier.

22. A method for treating hypertension in a mammal comprising administering to a mammal suffering from hypertension an effective amount for treating hypertension of the compound of formula (I) as recited in claim 1.

23. A method for treating edema in a mammal comprising administering to a mammal suffering from edema an effective amount for treating edema of the compound of formula (I) as recited in claim 1.

24. The method for the prevention or treatment of edema of claim 23 wherein said edema is congestive heart failure.

25. A compound of the formula (II):

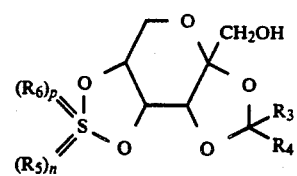

wherein $R_3$ and $R_4$ are the same or different and are hydrogen, $C_1$-$C_6$ alkyl, or are taken together to form a cyclopentyl or cyclohexyl ring; with the proviso that $R_3$ and $R_4$ both can not be methyl at the same time;

wherein n equals zero or one and p equals zero or one, provided that n and p are not both equal to zero at the same time;

and wherein $R_5$ and $R_6$ are oxygen or $NR_7$, where $R_7$ is hydrogen, $C_1$-$C_4$ alkyl, $C_1$-$C_4$ perfluoroalkyl, arenesulfonyl, lower alkoxycarbonyl or benzyloxycarbonyl.

26. A compound of the formula (III):

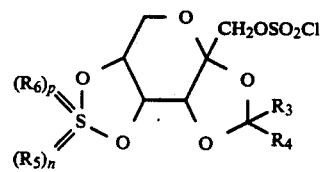

wherein $R_3$ and $R_4$ are the same or different and are hydrogen, $C_1$-$C_6$ alkyl, or are taken together to form a cyclopentyl or cyclohexyl ring;

wherein n equals zero or one and p equals zero or one, provided that n and p are not both equal to zero at the same time;

and wherein $R_5$ and $R_6$ are oxygen or $NR_7$, where $R_7$ is hydrogen, $C_1$-$C_4$ alkyl, $C_1$-$C_4$ perfluoroalkyl, arenesulfonyl, lower alkoxycarbonyl, or benzyloxycarbonyl.

27. A compound of claim 27 wherein said compound of the formula (III) is 2,3-O-(1-methylethylidene)-4,5-O-sulfonyl-$\beta$-D-fructopyranose chlorosulfate.

28. A compound of the formula (VI):

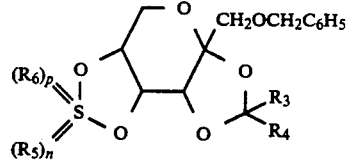

wherein $R_3$ and $R_4$ are the same or different and are hydrogen, $C_1$-$C_6$ alkyl, or are taken together to form a cyclopentyl or cyclohexyl ring;

wherein when n or p equals zero designates a lone pair of electrons;

wherein n equals zero or one and p equals zero or one, provided that n and p are not both equal to zero at the same time;

and wherein $R_5$ and $R_6$ are oxygen or $NR_7$, where $R_7$ is hydrogen, $C_1$-$C_4$ alkyl, $C_1$-$C_4$ perfluoroalkyl, arenesulfonyl, lower alkoxycarbonyl, benzyloxycarbonyl.

29. The compound of claim 28, wherein said compound of formula (VI) is 2,3-O-(1-methylethylidene)-1-O-phenylmethyl-4,5-O-sulfonyl-$\beta$-D-fructopyranose.

* * * * *